US006951731B2

(12) United States Patent
Northrop

(10) Patent No.: US 6,951,731 B2
(45) Date of Patent: Oct. 4, 2005

(54) METHOD FOR EVALUATING INHIBITION OF ASPARTIC PROTEASES

(75) Inventor: Dexter B. Northrop, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 468 days.

(21) Appl. No.: 10/166,461

(22) Filed: Jun. 10, 2002

(65) Prior Publication Data

US 2003/0049710 A1 Mar. 13, 2003

Related U.S. Application Data

(60) Provisional application No. 60/296,998, filed on Jun. 8, 2001.

(51) Int. Cl.$^7$ .......................... C12Q 1/37; G01N 33/573
(52) U.S. Cl. ........................................... 435/23; 435/7.4
(58) Field of Search ..................................... 435/23, 7.4

(56) References Cited

PUBLICATIONS

Lin et al. Correlations of the Basicity of His 57 with Transition State Analogue Binding, Substrate Reactivity, and the Strenght of the Low–Barrier Hydrogen Bond in Chymotrypsin. Biochemistry. 1998. vol. 37, pp. 11940–11948.*
Mildvan et al. Nuclear Magnetic Resonance Methods for the Detection and Study of Low–Barrier Hydrogen Bonds on Enzymes. 1999. vol. 308, pp. 219–245.*
Amagase, S., Nakayama, S. and Tsugita, A. Acid protease in Nepenthes. II. Study on the specificty of nepenthesin. J. Biochem. (Tokyo) 66 (1969) 431–439.
Amagase, S. Digestive enzymes in insectivorous plants. III. Acid proteases in the genus Nepenthes and *Drosera peltata*. J. Biochem. (Tokyo) 72 (1972) 73–81.
Ammerer, G., Hunter, C.P., Rothman, J.H., Saari, G.C., Valls, L.A. and Stevens, T.H. PEP4 gene of *Saccharomyces cerevisiae* encodes proteinase A, a vacuolar enzyme required for processing of vacuolar precursors. Mol. Cell. Biol. 6 (1987) 2490–2499.
Arima, K., Yu, J. and Iwasaki, S. Milk–clotting enzyme from *Mucor pusillus* var. *lindt*. Methods Enzymol. 19 (1970) 446–459.
Asakura, T., Watanabe, H., Abe K. and Arai, S. Rice aspartic proteinase, oryzasin, expressed during seed ripening and germination, has a gene organization distinct from those of animal and microbial aspartic proteinases. Eur. J. Biochem. 232 (1995) 77–83.
Azuma, T., Pals, G., Mlhandas, T.K., Couvreur, J.M. and Taggart, R.T. Human gastric cathepsin E. Predicted sequence, localization to chromosome 1, and sequence homology with other aspartic proteinases. J. Biol. Chem. 264 (1989) 16748–16753.
Balbaa, M., Blum, M., Hofmann, T. Mechanism of pepsin–catalyzed amino–transpeptidation reactions. *Int. J. Biochem.* 1994, 26, 35–42.

Barkholt, V. Amino acid sequence of endothiapepsin. Complete primary structure of the aspartic protease from *Endothia parasitica*. Eur. J. Biochem. 167 (1987) 327–338.
Barrett, A.J. Cathespin D and other carboxyl proteinases. In Proteinases in Mammalian Cells and Tissues (Barrett, A.J., ed.) p. 209–248 (1977) Elsevier/North–Holland, Amsterdam and London.
Baudyš, M., Foundling, S., Pavlik, M., Blundell, T. and Kostka, V. Protein chemical characterization of *Mucor pusillus* aspartic proteinase. Amino acid sequence homology with the other aspartic proteinases, disulfide bond arrangement and site of carbohydrate attachment. FEBS Lett. 235 (1988) 271–274.
Cawley, N.X., Chen,, H.C., Beinfeld, M.C. and Loh, Y.P. Specificity and kinetic studies on the cleavage of various prohormone mono– and paired–basic residue sites by yeast aspartic protease 3. J. Biol. Chem. 271 (1996) 4168–4176.
Chang, W.–J., Horiuchi, S., Takahashi, K., Yamasaki, M. and Yamada, Y. The structure and function of acid proteases. VI. Effects of acid protease–specific inhibitors on the acid proteases from *Aspergillus niger* var. *macrosporus*. J. Biochem. (Tokyo) 80 (1976) 975–981.
Cho, Y.K., Rebholz, K.L., Northrop, D.B. Solvent isotope effects on the onset of inhibition of porcine pepsin by pepstatin. *Biochemistry.* 1994, 33, (32):9637–42.
Cho, Y.K., Northrop, D.B. Transpeptidation by porcine pepsin catalyzed by a noncovalent intermediate unique to its iso–mechanism, *J. Biol. Chem.* 1999, 273, 24305–24308.
Cho, Y.K., Northrop, D.B. Effects of high pressure on solvent isotope effects of yeast alcohol dehydrogenase. *Biophys. J.* 2000, 79, 1621–1628.
Cleland, W.W. The use of isotope effects in the detailed analysis of catalytic mechanisms of enzymes. *Bioorg. Chem.* 1987, 15, 283–302.
Cleland, W.W. Low barrier hydrogen bonds in enzymatic catalysis. *Arc. Biochem. Biophys.* 2000, 382, 1–5.
Conner, G.E. Isolation of procathepsin D from mature cathepsin D by pepstatin affinity chromatography. Autocatalytic proteolysis of the zymogen form of the enzyme. Biochem. J. 263 (1989) 601–604.

(Continued)

*Primary Examiner*—Christopher R. Tate
*Assistant Examiner*—Marcela M Cordero Garcia
(74) *Attorney, Agent, or Firm*—Joseph T. Leone, Esq.; DeWitt Ross & Stevens S.C.

(57) ABSTRACT

Disclosed is a method for evaluating enzyme inhibitory activity of a known or putative inhibitor or modulator of an enzyme. The enzymes under investigation are those having a low-barrier hydrogen bond present in an active site of the enzyme. The compound whose activity is to be evaluated is contacted to an enzyme having a low-barrier hydrogen bond present in an active site of the enzyme. The presence, absence, or electronic character of the low-barrier hydrogen bond is then measured. The method is useful for designing mechanistic-based inhibitors or modulators of aspartic proteases and other enzymes.

17 Claims, 8 Drawing Sheets

PUBLICATIONS

Cooper, J., Foundling, S., Hemmings, A., Blundell, T., Jones, D.M., Hallett, A. and Szelke, M. The structure of a synthetic pepsin inhibitor complexed with endothiapepsin. Eur. J. Biochem. 169 (1987) 215–221.

Dame, J.B., Reddy, G.R., Yowell, C.A., Dunn, B.M., Kay, J. and Berry, C. Sequence, expression and modelled structure of an aspartic proteinase from the human malaria parasite *Plasmodium falciparum*. Mol. Biochem. Parasitol. 64 (1994) 177–190.

Davidson, R., Gertler, A. and Hofmann, T. *Aspergillus oryzae* acid proteinase. Purification and properties, and formation of p–chymotrypsin. Biochem. J. 147 (1975) 45–53.

Davies, D.R. The structure and function of the aspartic proteinases. Annu. Rev. Biophys. Biophys. Chem. 1990, 19, 189–215.

Dev, I.K. and Ray P.H. Signal peptidases and signal peptide hydrolases. J. Bioenerg. Biomembr. 22 (1990) 271–290.

Dunn, B.M. Human immunodeficiency virus 1 retropepsin. In: Handbook of Proteolytic Enzymes (Barrett, A.J., Rawlings, N.D. and Woessner, J.F. eds), pp. 919–928 (1998). Academic Press, London.

Emi, S., Mmyers D.V. and Iacobucci G.A. Purification and properties of the thermostable acid protease of *Penicillium duponti*. Biochemistry 15 (1976) 842–848.

Estivariz, F.E., Birch, N.P. and Loh, Y.P. Generation of Lys–g3–melanotropin from pro–opiomelanocortin1–77 by a bovine intermediate lobe secretory vesicle membrane–associated aspartic protease and purified pro–opiomelanocortin converting enzyme. J. Biol. Chem. 264 (1989) 17796–17801.

Faust, P.L., Kornfeld, S. and Chirgwin, J.M. Cloning and sequence analysis of cDNA for human cathepsin D. Proc. Natl Acad. Sci. USA 82 (1985) 4910–4914.

Foltmann, B. A review of prorennin and rennin. C. R. Trav. Lab. Carlsberg 35 (1966) 143–231.

Foltmann, R. Gastric proteinases–structure, function, evolution and mechanism of action. Essays Biochem. 17 (1981) 52–84.

Foltmann, B. and Jensen, A.L. Human progastricsin—analysis of intermediate during activation into gastricsin and determination of the amino–acid sequence of the propart. Eur. J. Biochem. 128 (1982) 63–70.

Francis, S.E., Gluzman, I.Y., Oksman, A., Knickerbocker, A., Mueller, R., Bryant, M.L., Sherman, D.R., Russell, D.G. and Goldberg, D.E. Molecular characterization and inhibition of a *Plasmodium falciparum* aspartic hemoglobinase. EMBO J. 13 (1994) 306–317.

Fruton, J.S. Aspartyl proteinases. In New Comprehensive Biochemistry vol. 16, Hydrolytic Enzymes (Neuberger, A. and Brocklehurst, K., eds), pp. 1–38 (1987) Elsevier, Amsterdam.

Fuller, R.S. Yapsin 2. In: Handbook of Proteolytic Enzymes, (Barrett, A.J., Rawlings, N.D. Woessner, J.F. eds), pp. 908–909 (1998) Academic Press, London.

Garg, G.K. and Virupaksha, T.K. Acid protease from germinated sorghum. 2. Substrate specificity with synthetic peptides and ribonuclease A. Eur. J. Biochem. 17 (1970) 4–12.

Gerritzen, D., Limbach, H.H., Kinetic isotope effects and tunneling in cyclic double and triple proton–transfer between acetic acid and methanol in tetrahydrofuran studied by dynamic H–1 and H–2 NMR spectroscopy*JACS* 1984, 869–879.

Gillespie, A.L., *The Natural History of Digestion*, London, 1898. (Copy not provided).

Gluzman, I.Y., Francis, S.E., Oksman, A., Smith, C.E., Duffin, K.L. and Goldberg, D.E. Order and specificity of the *Plasmodium falciparum* hemoglobin degradation pathway. J. Clin. Invest. 93 (1994) 1602–1608.

Goldberg, D.E., Slater, A.F.G., Beavis, R., Chait, B., Cerami, A. and Henderson, G.B. Hemoglobin degradation in the human malaria pathogen *Plasmodium falciparum:* a catabolic pathway initiated by a specific aspartic protease. J. Exp. Med. 173 (1991) 961–969.

Goldman, R.C., Frost, D.J., Capobianco, J.O., Kadam, S., Rasmussen, R.R., Abad–Zapatero C. Antifungal drug targets: Candida secreted aspartyl protease and fungal wall beta–glucan synthesis. Infect. Ag. Dis. 1995, 4, 228–47.

Harris, T.J.R., Lowe, P.A., Lyons, A., Thomas, P.G., Eaton, M.A.W., Millican, T.A., Patel, T.P., Bose, C.C., Carey, N.H. and Doel, M.T. Molecular cloning and nucleotide sequence of cDNA coding for calf preprochymosin. Nucleic Acids Res. 10 (1982) 2177–2187.

Hata, T., Hayashi, R. and Dot, E. Purification of yeast proteinases. Part III. Isolation and physicochemical properties of yeast proteinase A and C. Agric. Biol. Chem. 31 (1967) 357–367.

Hayano, T., Sogawa, K., Ichihara, Y., Fujii–Kuriyama, Y. and Takahasi, K. Primary structure of human pepsinogen C gene. J. Biol. Chem. 263 (1988) 1382–1385.

Henney, H.R. and Tavanna G. Purification and some properties of an intracellular acid (carboxyl) proteinase from differentiating haploid cells of *Physarum flavicomum*. Exp. Mycol. 6 (1982) 161–170.

Hill, J., Tyas, L., Phylip, L.H., Kay, J., Dunn, B.M. and Berry, C. High level expression and characterisation of plasmepsin II, an aspartic proteinase from *Plasmodium falciparum*. FEBS Lett. 352 (1994) 155–158.

Hofmann, T. Penicillopepsin. Methods Enzymol. 45 (1976) 434–450.

Hofmann, T., Blum, M., Cunningham, A. Studies on the mechanism of action of penicillopepsin. Adv. Exp. Med. Biol. 1991, 608, 243–54.

Hsu, I.–N., Delbaere, L.T.J., James, M.N.G. and Hofmann, T. Penicillopepsin from *Penicillium janthinellum* crystal structure at 2.8 Å and sequence homology with porcine pepsin. Nature 266 (1977) 140–144.

Hunkapillar, M.W., Richards, J.H. Studies on the catalytic mechanism of pepsin using a new synthetic substrate. *Biochemistry*, 1972, 273, 2829–2839.

Hyland, L.J., Tomaszek, T.A., Jr., and Meek, T.D. Human immunodeficiency virus HIV–1 protease. 2. Use of pH rate studies and solvent kinetic isotope effects to elucidate details of chemical mechanism. *Biochemistry*, 1991, 30, 8454–8463.

Ichihara, S. and Uchino, F. The specificity of acid proteinase from Acrocylindrium. Agric. Biol. Chem. 39 (1975) 423–428.

Ichishima, E., Kumagai, H. and Tomoda, K. Substrate specificity of carboxyl proteinase from *Pycnoporus coccineus*, a wood–deteriorating fungus. Curr. Microbiol. 3 (1980) 333–337.

Ilo, K. and Yamasaki, M. Specificity of acid proteinase A from *Aspergillus niger* var. macrosporus towards B–chain of performic acid oxidized bovine insulin. Biochim. Biophys. Acta 429 (1976) 912–924.

Inagami, T. and Murakami, K. Pure renin. Isolation from hog kidney and characterization. J. Biol. Chem. 252 (1977) 2978–2983.

Inagami, T. Structure and function of renin. J. Hypertension 7 (Suppl. 2) (1989) S3–S8.

James, M.N.G. and Sielecki, A.R. Molecular structure of an aspartic proteinase zymogen, porcine pepsinogen, at 1.8 Å resolution. Nature 319 (1986) 33–38.

Jupp, R.A., Richards, A.D., Kay, J., Dunn, B.M., Wyckoff, J.B., Samloff, I.M. and Yamamoto, K. Identification of the aspartic proteinase from human erythrocyte membranes and gastric mucosa (slow–moving proteinase) as catalytically equivalent to cathepsin E. Biochem. J. 254 (1988) 895–898.

Kamada, M., Oda, K. and Murao, S. The purification of the extracellular acid protease of *Rhodotorula glutinis* K–24 and its general properties. Agric. Biol. Chem. 36 (1972) 1095–1101.

Kervinen, J., Sarkkinen, P., Kalkkinen, N., Mikola, L. and Saarma, M. Hydrolytic specificity of the barley grain aspartic proteinase. Phytochemistry 32 (1993) 799–803.

Kervinen, J., Törmäkangas, K., Runeberg–Roos, P., Guruprasad, K., Blundell, T. and Teeri, T.H. Structure and possible function of aspartic proteinases in barley and other plants. Adv. Exp. Med. Biol. 62 (1995) 241–254.

Knowles, J.R. On the mechanism of action of pepsin. *Phil. Trans. Royal Soc. Lon.—Ser. B: Biol. Sci.* 1970, 257, 135–46.

Kobayashi H., Kusakabe, I. and Murakami, K. Substrate specificity of a carboxyl proteinase from *Irpex lacteus*. Agric. Biol. Chem. 47 (1983) 1921–1923.

Kobayashi, H., Sekibata, S., Shibuya, H., Yoshida, S., Kusakabe, I. and Murakami, K. Cloning and sequence analysis of cDNA for *Irpex lacteus* aspartic proteinase. Agric. Biol. Chem. 53 (1989) 1927–1933.

Kobayashi, H., Kusakabe, I. and Murakami, K. Purification and characterization of a pepstatin–insensitive carboxyl proteinase from *Polyporus tulipiferae* (*Irpex lacteus*). Agric. Biol. Chem. 49 (1985) 2393–2397.

Kovaleva, G.G., Shimanskaya, M.P. and Stepanov, V.M. The site of diazoacetyl inhibitor attachment to acid proteinase of *Aspergillus awamori*—an analog of penicillopepsin and pepsin. Biochem. Biophys.Res. Commun. 49 (1972) 1075–1982.

Kresge, A. J. Solvent isotope effect in $H_2O–D_2O$ mixures. *Pure Applied Chem.* 1964, 8, 243–258.

Kuo, L.C. and Shafer, J.A. (eds) Retroviral Proteases. Methods Enzymol. 241 (1994) 1–431 (Copy not provided).

Kurono, Y., Chidimatsu, M., Horikoshi, K. and Ikeda, Y. Isolation of a protease from a Rhizopus product. Agric. Biol. Chem. 35 (1971) 1668–1675.

Lapresle, C., Puizdar, V., Porchon–Bertolotto, C., Joukoff, E. and Turk, V. Structural differences between rabbit cathepsin E and cathepsin D. Biol. Chem. Hoppe–Seyler 367 (1986) 523–526.

Lee, D. and Ryle, A.P. Pepsinogen D. A fourth proteolytic zymogen from pig gastric mucosa. Biochem. J. 104 (1967) 735–741.

Lee, D. and Ryle, A.P. Pepsin D. A minor component of commercial pepsin preparations. Biochem. J. 104 (1967) 742–748.

Lin, X. and Tang, J. Thermopsin. Methods Enzymol. 248 (1995) 156–168.

Loh, Y.P., Parish, D.C. and Tuteja, R. Purification and characterization of a paired basic residue–specific pro–opiomelanocortin converting enzyme from bovine pituitary intermediate lobe secretory vesicles. J. Biol. Chem. 260 (1985) 7194–7205.

Loh, Y.P. Kinetic studies on the processing of human b–lipotropin by bovine pituitary intermediate lobe pro–opiomelanocortin–converting enzyme. J. Biol. Chem. 261 (1986) 11949–11955.

Lott, T.J., Page, L.S., Boiron, P., Benson, J. and Reiss, E. Nucleotide sequence of the *Candida albicans* aspartyl proteinase gene. Nucleic Acids Res. 17 (1989) 1779 only.

Mackay, V.L., Welch, S.K., Insley, M.Y., Manney, T.R., Holly, J., Saari, G.C. and Parker, M.L. The *Saccharomyces cerevisiae* BAR1 gene encodes an exported protein with homology to pepsin. Proc. Natl. Acad. Sci. USA 85 (1988) 55–59.

Mackay, V.L., Armstrong, J., Yip, C., Welch, S., Walker, K., Osborn, S., Sheppard, P. and Forstrom, J. Characterization of the bar proteinase, an extracellular enzyme from the yeast *Saccharomyces cerevisiae*. Adv. Exp. Med. Biol. 306 (1991) 161–172.

Mains, G., Takahashi, M., Sodek, J. and Hofmann, T. The specificity of penicillopepsin. Can. J. Biochem. 49 (1971) 1134–1149.

Maita, T., Nagata, S., Matsuda, G., Maruta, S., Oda, K., Murao, S. and Tsuru, D. Complete amino acid sequence of *Scytalidium lignicolum* acid protease B. J. Biochem. (Tokyo) 95 (1984) 465–473.

Majima, E., Oda, K., Murao, S. and Ichishima, E. Comparative study on the specificities of several fungal aspartic and acidic proteinase towards the tetradecapeptide of a renin substrate. Agric. Biol. Chem. 52 (1988) 787–793.

Martin, P., Trieu–Cuot, P., Collin, J.–C. and Ribadeau Dumas, B. Purification and characterization of bovine gastricsin. Eur. J. Biochem. 122 (1982) 31–39.

Meek, T.D. Catalytic mechanisms of the aspartic proteinases. In *Comprehensive Biological Catalysis: a Mechanistic Reference,* Sinnott, M., Ed., Academic Press: San Diego, 1998; Chapter 8.

Meussdoerffer, F., Tortora, P. and Holzer, H. Purification and properties of proteinase A from yeast. J. Biol. Chem. 255 (1980) 12087–12093.

Mihalyi, E. *Application of Proteolytic Enzymes to Protein Structure Studies.* CRC Press, Cleveland, OH, 1972, pp. 39–101.

Morihara, K. and Oka, T. Comparative specificity of microbial acid proteinases for synthetic peptides. III. Relationship with their trypsinogen activating ability. Arch. Biochem. Biophys. 157 (1973) 561–572.

Murao, S., Funakoshi, S. and Oda, K. Purification, crystallization and some enzymatic properties of acid protease of *Cladosporium* sp. No. 45–2. Agric. Biol. Chem. 36 (1972) 1327–1333.

Murakami–Murofushi, K., Hiratsuka, A. and Ohta, J. A novel acid protease from haploid amoebae of *Physarum polycephalum,* and its changes during mating and subsequent differentiation into diploid plasmodia. Cell Struct. Funct. 9 (1984) 311–315.

Murakami–Murofushi, K., Takahashi, T., Minowa, Y., Iino, S., Takeuchi, T., Kitagaki–Ogawa, H., Murofushi, H. and Takajashi, K. Purification and characterization of a novel intracellular acid proteinase rom the plasmodia of a true slime mold, *hysarumolycephalum*. J. Biol. Chem. 265 (1990) 19898–19903.

Negi, M., Tsuboi, R., Matsui, T. and Ogawa, H. Isolation and characterization of proteinase from *Candida albicans* substrate specificity. J. Invest. Dermatol. 83 (1984) 32–36.

Neumann, H., Levin, H., Berger, A., Katchalski, E. Pepsin–catalyzed transpeptidation of the amino–transfer type. *Biochem. J.* 1959, 73, 33–41.

Neumann, H., Knowles, J.R. Acyl– and amino–transfer routes in pepsin–catalyzed reactions. *J. Am. Chem. Soc.* 1975, 97, 3557–3559.

North, M.J. and Whyte, A. Purification and characterization of two acid proteinases from *Dictyostelium discoideum*. J. Gen. Microbiol. 130 (1984) 123–134.

Northrop, J.H. Crystalline pepsin. I. Isolation and tests for purity, *J. Gen. Physiol.* 1930, 739–766.

Northrop, D.B. On the meaning of $K_m$ and $V_{max}/K_m$ in enzyme kinetics. *J. Chem. Ed.* 1998. 75. 1153–57.

Oda, K., Kamada, M. and Murao, S. Some physicochemical properties and substrate specificity of acid protease of *Rhodotorula glutinis* K–24. Agric. Biol. Chem. 36 (1972) 1103–1108.

Oda, K. Funakoshi, S. and Murao, S. Some physicochemical properties and substrate specificity of acid protease isolated from Cladosporium sp. No. 45–2. Agric. Biol. Chem. 37 (1973) 1723–1729.

Oda, K. and Murao, S. Purification and some enzymatic properties of acid protease A and B of *Scytalidium lignicolum* ATCC 25468. Agric. Biol. Chem. 38 (1974) 2435–2444.

Oda, K. and Murao, S. Action of *Scytalidium lignicolum* acid proteases on insulin B–chain. Agric. Biol. Chem. 40 (1976) 1221–1225.

Oda, K. Torishima, H. and Murao, S. Purification and characterization of acid proteinase C of *Scytalidium lignicolum* ATCC 24568. Agric. Biol. Chem. 50 (1986) 651–658.

Oda, K., Nakazima, T., Terashita, T., Suzuki, K. and Murao, S. Purification and properties of an S–PI(pepstatin Ac)–insensitive carboxyl proteinase from a Xanthomonas sp. bacterium. Agric. Biol. Chem. 51 (1987) 3073–3080.

Oda, K., Sugitani, M., Fukuhara, K. and Murao, S. Purification and properties of a pepstatin–insensitive carboxyl proteinase from a Gram–negative bacterium. Biochim. Biophys. Acta 923 (1987) 463–469.

Oda, K., Fukuda, Y., Murao, S., Uchida, K., and Kainosho, M. A novel proteinase inhibitor, tyrostatin, inhibiting some pepstatin–insensitive carboxyl proteinases. Agric. Biol. Chem. 53 (1989) 405–415.

Oda, K. and Murao, S. Pepstatin–insensitive carboxyl proteinases. In Structure an Function of Aspartic Proteinases (Dunn, B.M., ed.), pp. 185–201 (1991) Plenum Press, New York.

Oda, K., Nakatani, H. and Dunn, B.M. Substrate specificity and kinetic properties of pepstatin–insensitive carboxyl proteinase from Pseudomonas sp. No. 101. Biochim. Biophys. Acta 1120 (1992) 208–214.

Ohtsuru, M., Tang, J. and Delaney, R. Purification and characterization of rhizopuspesin isozymes from a liquid culture of *Rhizopus chinesis*. Int. J. Biochem. 14 (1982) 925–932.

Oka, T., Ishino, K., Tsuzuki, H., Morihara, K. and Arima, K. On the specificity of a rennin–like enzyme from *Mucor pusillus*. Agric. Biol. Chem. 37 (1973) 1177–1184.

Olsen, V., Guruprasad, K., Cawley, N.X., Chen, H.C., Blundell, T.L. and Loh, Y.P. Cleavage efficiency of the novel aspartic protease yapsin 1 (Yap3p) enhanced for substrates with arginine residues flanking the P1 site: correlation with electronegative active–site pockets predicted by molecular modeling. Biochemistry 37 (1998) 2768–2777.

Ostoslavskaya, V.I., Kotlova, E.K., Stepanov, V.M., Rudenskaya, G.H., Baratova, L.A. and Belyanova, L.P. Aspergillopepsin F–A carboxylic proteinase from *Aspergillus foetidus*. Bioorg. Khim. 5 (1976) 595–603.

Ostoslavskaya, V.I., Revina, L.P., Kotlova, E.K., Surova, I.A., Levin, E.D., Timokhima, E.A. and Stwpanov, V.M. The primary structure of aspergillopepsin A, aspartic proteinase A, aspartic proteinase from *Aspergillusawamori*. IV. Amino acid sequence of the enzyme. Bioorg. Khim. 12 (1986) 1030–1047.

Ottesen, M. Rickert, W. The acid protease of *Mucor miehei*. Methods Enzymol. 19 (1970) 459–460.

Panneerselvam, M. and Dhar, S.C. Studies of the peptide bond specificity and the essential groups of an acid proteinase from *Aspergillus fumigatus*. Ital. J. Biochem. 30 (1981) 207–216.

Piana, S.; Carloni, P. Conformational flexibility of the catalytic asp dyad in HIV–1 protease: an ab initio study on the free enzyme. *Prot. Struct. Func. Gen.* 2000, 39, 26–36.

Piana, S, Sebastiani, D., Carloni, P., Parrinello, M. An ab–initio molecular dynamics–based assignment of the protonation state of pepstatin A/HIV–1 protease cleavage site. *J. Am. Chem. Soc.* 2001, manuscript submitted.

Pohl, J. and Dunn, B.M. Secondary enzyme–substrate interactions: kinetic evidence for ionic interactions between substrate side chains and the pepsin active site. Biochemistry 27 (1988) 4827–4834.

Quinn, D.M., Sutton, L.D., Theroetical basis and mechanistic utility of solvent isotope effects. In *Enzyme Mechanism from Isotope Effects*, P. F. Cook, editor. CRC Press, 1991, 73–126.

Rebholz, K.L., Northrop, D.B. Slow step after bond–breaking by porcine pepsin identified using solvent deuterium isotope effects, *Biochem. Biophys. Res. Commun.* 1991, 176, 65–69.

Rebholz, K.L., *Enzymatic iso mechanisms: alanine racemase, fumarase, and aspartic proteinases*. University of Wisconsin–Madison, 1993.

Reid, W.A., Vongsorasak, L., Svasti, J., Valler, M.J. and Kay J. Identification of the acid proteinase in human seminal fluid as a gastricsin originating in the prostate. Cell Tissue Res. 236 (1984) 597–600.

Remold, H., Fasold, H. and Staib, F. Purification and characterization of a proteolytic enzyme from *Candida albicans*. Biochim. Biophys. Acta 167 (1968) 399–406.

Rodriquez, E.J., Meek, T.D. (Unpublished results).

Rodriquez, E.J., Angeles, T.S., Meek, T.D. Use of nitrogen–15 kinetic isotope effects to elucidate details of the chemical mechanism of human immunodeficiency virus 1 protease. *Biochemistry* 1993, 32, 12380–12385.

Rüchel, R. Properties of a purified proteinase from the yeast *Candida albicans*. Biochim. Biophys. Acta 659 (1981) 99–113.

Runeberg–Roos, P., Törmäkangas, K. and Östman, A. Primary structure of a barley–grain aspartic proteinase. A plant aspartic proteinase resembling mammalian cathepsin D. Eur. J. Biochem. 202 (1991) 1021–1027.

Ryle, A.P. The porcine pepsins and pepsinogens. Methods Enzymol. 19 (1970) 316–336.

Sankaran, K. and Wu, H.C. Bacterial prolipoprotein signal peptidase. Methods Enzymol. 248 (1995) 169–180.

Sawada, J. Studies on the acid–protease of *Paecilomyces varioti* Bainier TPR–220. Part I. Crystallization of the acid–protease of *Paecilomyces varioti* Bainier TPR–220. Agric. Biol. Chem. 27 (1963) 677–683.

Sawada, J. The acid–protease of *Paccilomyces varioti*. III. The specificity of the crystalline acid–protease on synthetic substrates. Agric. Biol. Chem. 28 (1964) 869–875.

Shinano, S. and Fukushima, K. Studies on the lotus seed protease. Part III. Some physicochemical and enzymatic properties. Agric. Biol. Chem. 35 (1971) 1488–1494.

Sielecki, A.R., Hayakawa, K., Fujinaga, M., Murphy, M.E.P., Fraser, M., Muir, A.K., Carilli, C.T., Lewicki, J.A., Baxter, J.D. and James, M.N.G. Structure of recombinant human renin, a target for cardiovascular–active drugs, at 2.5 Å resolution. Science 243 (1989) 1346–1351.

Slater, E.E. Renin. Methods Enzymol. 80 (1981) 427–442.

Smith, R., Brereton, I.M., Chai, R.Y., Kent, S.B., Ionization states of the catalytic residues in HIV–1 protease. *Nature Struc. Biol. 1996*, 3, 946–50.

Sörensen, S.P.L. Enzymstudien II. Mitteilung. Über die Messung und die Bedeutung der Wasserstoffionen—konzentration bei enzymatischen Prozessen, *Biochem. Zeit.* 1909, 21, 201–304.

Sternberg, M. Bond specificity, active site and milk cloting mechanism of the *Mucor miehei* protease, Biochim. Biophys. Acta 285 (1972) 383–392.

Suguna, K., Padlan, E.A., Smith, C.W., Carlson, W.D. and Davies, D.R. Binding of a reduced peptide inhibitor to the aspartic proteinase from *Rhizopus chinesis:* implications for a mechanism of action. Proc. Natl Acad. Sci. USA 84 (1987) 7009–7013.

Sutcliffe, M.J., Nigel S. Scrutten, N.S. Enzyme catalysis: over–the–barrier or through–the–barrier? *Trends Biochem. Sci.* 2000, 25, 405–408.

Takahashi, K., Chang, W–J. and Ko, J–S. Specific inhibition of acid proteases from brain, kidney, skeletal muscle, and insectivorous plants by diazoacetyl–DL–norleucine methyl ester and by pepstatin. J. Biochem. (Tokyo) 76 (1974) 897–899.

Takahashi, K. and Chang, W.–J. The structure and function of acid proteases. V. Comparative studies on the specific inhibition of acid proteases by diazoacetyl–DL–norleucine methyl ester, 1,2–epoxy–3–(p–nitrophenoxy)propane and pepstatin. J. Biochem. (Tokyo) 80 (1976) 497–506.

Takahashi, T. and Tang, J. Cathepsin D from porcine and bovine spleen. Methods Enzymol. 80 (1981) 565–581.

Tanaka, N., Takeuchi, M. and Ichishima, E. Purification of an acid proteinase from *Aspergillus saitoi* and determination of peptide bond specificity. Biochim. Biophys. Acta 485 (1977) 406–416.

Tang, J. Gastricsin and pepsin. Methods Enzymol. 19 (1970) 406–421.

Tang, J. and Wong, R.N.S. Evolution in the structure and function of aspartic proteases. J. Cell. Biochem. 33 (1987) 53–63.

Terashita, T., Oda, K., Kono, M. and Murao, S. *Streptomyces pepsin* inhibitor–insensitive carboxyl proteinase from *Lentinus edodes.* Agric. Biol. Chem. 45 (1981) 1937–1943.

Terashita, T., Oda, K., Kono, M. and Murao, S. *Streptomyces pepsin* inhibitor–insensitive carboxyl proteinase from *Ganoderma lucidum.* Agric. Biol. Chem. 48 (1984) 1029–1035.

Tökès, Z.A., Woon, W.C. and Chambers, S.M. Digestive enzymes secreted by the carnivorous plant *Nepenthes macferlani* L. Planta 119 (1974) 39–46.

Tomoda, K. and Shimazono, H. Acid protease produced by *Trametes sanguinea* a wood–destroying fungus. Part I. Purification and crystallization of the enzyme. Agric. Biol. Chem. 28 (1964) 770–773.

Tsuru, D., Hattori, A., Tsuji, H., Yamamoto, T. and Fukumoto, J. Studies on mold proteases. Part II. Substrate specificity of acid protease of *Rhizopus chinensis.* Agric. Biol. Chem. 33 (1969) 1419–1426.

Tsuru, D., Shimada, S., Maruta, S., Yoshimoto, T., Oda, K., Murao, S., Miyata, T. and Iwanaga, S. Isolation and amino acid sequence of a peptide containing an epoxide–reactive residue from the Thermolysin–digest of *Scytalidium lignicolum* acid protease B. J. Biochem. (Tokyo) 99 (1986) 1537–1539.

Turner, A.J., Murphy, L.J., Molecular pharmacology of endothelin converting enzymes. *Biochem. Pharmacol,* 1996, 51, 91–102.

Uchino, F., Kurono, Y. and Doi, S. Purification and some properties of crystalline acid protease from Acrocylindrium sp. Agric. Biol. Chem. 31 (1967) 428–434.

Vassar et al., Beta–secretase cleavage of Alzheimer's amyloid precursor protein by the transmembrane aspartic protease BACE, *Science,* 1999, 286, 735–41.

Visser, S., Slangen, C.J. and Van Rooijen P.J. Peptide substrates for chymosin (rennin). Interaction sites in k–casein–related sequences located outside the (103–108)–hexapeptide region that fits into the enzyme's active–site cleft. Biochem. J. 244 (1987) 553–558.

Whitaker, J.R. Protease of *Endothia parasitica.* Methods Enzymol. 19 (1970) 436–445.

Williams, D.C., Whitaker, J.R. and Caldwell, P.V. Hydrolysis of peptide bonds of the oxidized B–chain of insulin by *Endothia parasitica* protease. Arch. Biochem. Biophys. 149 (1972) 52–61.

Yagi, F., Fan, J., Tadera, K. and Kobayashi, A. Purification and characterization of carboxyl proteinase from *Aspergillus kawachii.* Agric. Biol. Chem. 50 (1986) 1029–1033.

Yonezawa, S., Fujii, K., Maejima, Y., Tamoto, K., Mori, Y. and Muto, N. Further studies on rat cathepsin E: subcellular localization and existence of the active subunit form. Arch. Biochem. Biophys. 267 (1988) 176–183.

Zevaco, C., Hermier, J. and Gripon, J.–C. Le système protéolytique de *Penicillium roqueforti.* II—Purification et propriétés de la protéase acide. Biochimie 55 (1973) 1353–1360.

Zhao, Q., Abeygunawardana, C., Gittis, A.G., Mildvan, A.S. Hydrogen bonding at the active site of 5–3–ketosteroid isomerase. *Biochemistry,* 1997, 36, 14616–14626.

Zhao, X.–J. and Wu, H.C. Nucleotide sequence of the *Staphylococcus aureus* signal peptidase II (lsp) gene. FEBS Lett. 299 (1992) 80–84.

* cited by examiner

METHOD FOR EVALUATING INHIBITION OF ASPARTIC PROTEASES

PRIORITY

Priority is hereby claimed to provisional application Ser. No. 60/296,998, filed Jun. 8, 2001, the entire contents of which is incorporated herein by reference.

FIELD OF THE INVENTION

The invention is directed to clinical and diagnostic methods for evaluating the efficacy of known and putative inhibitors of aspartic proteases.

BACKGROUND

Aspartic proteases have the longest recorded history in all of enzymology, and perhaps the most perplexing. The earliest reported aspartic protease is pepsin. Pepsin is also likely to be the first enzyme recognized as an active principle (in 1783) and given a name (in 1825). Pepsin is only the second enzyme to be extracted (in 1836) and the second enzyme to be crystallized (in 1930).[1, 2]

Extracts of pepsin have to be acidified to regain full activity, with different acids giving different results. Sörensen noted that if activities were plotted against hydrogen ion concentrations, the results were similar.[3] (By way of historical footnote, to solve his scaling problem, Sörensen employed a logarithmic abscissa—and thus invented pH).

In addition to their catalytic functionality (hydrolytic cleavage of protein and peptide substrates), the identifying characteristic of aspartic proteases is their wide bell-shaped pH profiles with acidic optima. This peculiar characteristic has never been fully accounted for despite being featured in Sörensen's 1909 report of pH-dependent kinetics. That long unaccounted for peculiarity is without precedent in enzymology and, moreover, is joined with other seemingly unrelated uncertainties.

For example, how can transpeptidation reactions involving both halves of a peptide substrate (implying covalent acyl- and amino-enzyme intermediates) be explained? The parallel existence of acyl- and amino-enzyme intermediates within a single enzymatic mechanism seemed unlikely.[4]

In the last two decades new uncertainties arose regarding aspartic proteases, most notably anomalous isotope effects. The discovery of these isotope effects was driven in large measure by the clinical significance of the HIV proteases. As the search for mechanism-based aspartic protease inhibitors for use in treating AIDS gained momentum, the mechanistic peculiarities of aspartic proteases came to the fore.

An excellent review of the current knowledge regarding aspartic proteases can be found in Meek.[6]

In a notable recent paper, an ab initio study of free HIV protease by Piana & Carloni[5], the authors describe the presence of a low-barrier hydrogen bond within the active site of HIV-1 protease (an aspartic protease). As described below, determining the presence or absence of this low-barrier hydrogen bond when the aspartic protease is exposed to a known or putative aspartic protease inhibitor can serve as an excellent means to predict the efficacy of the inhibitor. Thus, the present invention is drawn to a method for evaluating the inhibition of aspartic proteases based upon the presence, absence, and electronic character of the low-barrier hydrogen bond present in the active site of all aspartic proteases.

SUMMARY OF THE INVENTION

The invention is directed to a method for evaluating the enzyme inhibitory activity of a known or putative inhibitor or modulator of an enzyme having a low-barrier hydrogen bond present in an active site of the enzyme. It has been found that the ability of a compound to interfere with mobility (i.e. the electronic character) of the low-barrier hydrogen bond, or to break the bond, or to prevent breakage of the bond, is predictive of the inhibitory activity of the compound tested. A first embodiment of the invention comprises contacting a known or putative enzyme inhibitor or modulator to an enzyme having a low-barrier hydrogen bond present in an active site of the enzyme, in a medium and under conditions wherein the enzyme is active. Then, the presence, absence, or electronic character of the low-barrier hydrogen bond present in the active site of the enzyme is measured, whereby the enzyme inhibitory activity of the inhibitor or modulator is evaluated.

Preferably the enzyme under investigation is an aspartic protease or an enzyme having an enzyme classification of EC 3.4.23.x.

The presence, absence, or electronic character of the low-barrier hydrogen bond can be measured by means for measuring chemical bonds, such means generally being selected from the group consisting of proton NMR spectroscopy, UV spectrophotometry, IR spectrophotometry, visible spectrophotometry, fluorescence spectroscopy, and mass spectrometry. Proton NMR is preferred. The presence, absence, or electronic character of the low-barrier hydrogen bond can be measured by examining solvent isotope effects, or by generating a pH profile of a candidate inhibitor (i.e., plotting inhibitor activity versus pH). The preferential or exclusive binding of a known or putative enzyme inhibitor to a monoprotonated form of the enzyme can be determined from pH profiles of enzyme inhibition. Thus, the pH profile where the inhibitor binds to a low-barrier hydrogen bond will generally assume a standard bell shape. In contrast, where the inhibitor binds to some other form of the enzyme (or multiple forms of the enzyme), the pH profile will appear as a half-bell or flat.

Thus, in the preferred embodiment, the invention is directed to a method for evaluating the enzyme inhibitory activity of a known or putative inhibitor or modulator of an aspartic protease. The method comprises first contacting a known or putative inhibitor or modulator of an aspartic protease to an aspartic protease having a low-barrier hydrogen bond present in an active site of the aspartic protease, in a medium and under conditions wherein the aspartic protease is active. Then the presence, absence, or electronic character of the low-barrier hydrogen bond present in the active site of the aspartic protease is measured (preferably via NMR), whereby the enzyme inhibitory activity of the inhibitor or modulator is evaluated.

The subject invention is extremely useful in high-throughput screening of drug candidate compounds. As described herein, the low-barrier hydrogen bond present in the active site plays a critical role in the catalytic activity of many enzymes in general and aspartic proteases in particular. Thus, the present invention find use a tool to help design mechanistic-based inhibitors of aspartic proteases and other enzymes having a low-barrier hydrogen bond present in the active site.

BRIEF DESCRIPTION OF THE DRAWINGS

FIG. 6A depicts the entire sequence; FIGS. 6B and 6C combined depict the individual steps in greater detail.

DETAILED DESCRIPTION OF THE INVENTION

Figure 1:
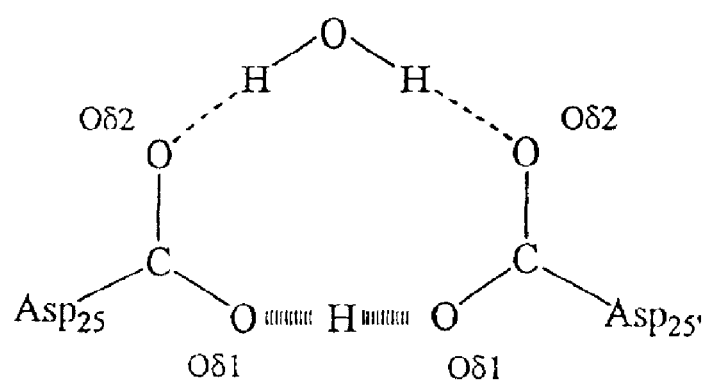
FIG. 1: Co-planar catalytic carboxyls of HIV-1 protease with a low barrier hydrogen bond between the Oδ1 oxygens and normal hydrogen bonds between a water molecule and the δO2 oxygens; after Piana & Carloni.[5]

Definitions:

Aspartic proteases (also known as aspartic endopeptidases) are classified as EC 3.4.23.x (where "x" is a numerical variable). As used herein, the term "aspartic protease(s)" explicitly encompasses all enzymes falling within enzyme classification EC 3.4.23.x, including, without limitation, the following enzymes:

EC 3.4.23.1 Pepsin A
EC 3.4.23.2 Pepsin B
EC 3.4.23.3 Gastricsin
EC 3.4.23.4 Chymosin
EC 3.4.23.5 Cathepsin D
EC 3.4.23.12 Nepenthesin
EC 3.4.23.15 Renin
EC 3.4.23.16 HIV-1 retropepsin
EC 3.4.23.17 Pro-opiomelanocortin converting enzyme
EC 3.4.23.18 Aspergillopepsin I
EC 3.4.23.19 Aspergillopepsin II
EC 3.4.23.20 Penicillopepsin
EC 3.4.23.21 Rhizopuspepsin
EC 3.4.23.22 Endothiapepsin
EC 3.4.23.23 Mucorpepsin
EC 3.4.23.24 Candidapepsin
EC 3.4.23.25 Saccharopepsin
EC 3.4.23.26 Rhodotorulapepsin
EC 3.4.23.27 Physaropepsin
EC 3.4.23.28 Acrocylindropepsin
EC 3.4.23.29 Polyporopepsin
EC 3.4.23.30 Pycnoporopepsin
EC 3.4.23.31 Scytalidopepsin A
EC 3.4.23.32 Scytalidopepsin B
EC 3.4.23.33 Xanthomonapepsin
EC 3.4.23.34 Cathepsin E
EC 3.4.23.35 Barrierpepsin
EC 3.4.23.36 Signal peptidase II
EC 3.4.23.37 Pseudomonapepsin
EC 3.4.23.38 Plasmepsin I
EC 3.4.23.39 Plasmepsin II
EC 3.4.23.40 Phytepsin
EC 3.4.23.41 Yapsin 1
EC 3.4.23.42 Thermopsin More specific details on each of these enzymes is as follows:

EC 3.4.23.1, pepsin A: Reaction: preferentially cleaves hydrophobic, preferably aromatic, residues in P1 and P1' positions. Cleaves Phe1Val, Gln4His, Glu13Ala, Ala14Leu, Leu15Tyr, Tyr16Leu, Gly23Phe, Phe24Phe, and Phe25Tyr bonds in the B chain of insulin. It is the predominant endopeptidase in the gastric juice of vertebrates, formed from pepsinogen A by limited proteolysis. Human pepsin A occurs in five molecular forms. Pig pepsin D is unphosphorylated pepsin A. References:

Lee, D. and Ryle, A. P. Pepsinogen D. A fourth proteolytic zymogen from pig gastric mucosa. Biochem. J. 104 (1967) 735–741. 2.

Lee, D. and Ryle, A. P. Pepsin D. A minor component of commercial pepsin preparations. Biochem. J. 104 (1967) 742–748.

Foltmann, R. Gastric proteinases—structure, function, evolution and mechanism of action. Essays Biochem. 17 (1981) 52–84.

James, M. N. G. and Sielecki, A. R. Molecular structure of an aspartic proteinase zymogen, porcine pepsinogen, at 1.8 Å resolution. Nature 319 (1986) 33–38.

Fruton, J. S. Aspartyl proteinases. In New Comprehensive Biochemistry Vol. 16, Hydrolytic Enzymes (Neuberger, A. and Brocklehurst, K., eds), pp. 1–38 (1987) Elsevier, Amsterdam.

Tang, J. and Wong, R. N. S. Evolution in the structure and function of aspartic proteases. J. Cell. Biochem. 33 (1987) 53–63.

Pohl, J. and Dunn, B. M. Secondary enzyme-substrate interactions: kinetic evidence for ionic interactions between substrate side chains and the pepsin active site. Biochemistry 27 (1988) 4827–4834.

EC 3.4.23.2, pepsin B: Reaction: Degradation of gelatin; little activity on hemoglobin. Specificity on B chain of insulin more restricted than that of pepsin A; does not cleave at Phe1-Val, Gln4-His or Gly23-Phe. References:

Ryle, A. P. The porcine pepsins and pepsinogens. Methods Enzymol. 19 (1970) 316–336.

EC 3.4.23.3, gastricsin (pepsin C): Reaction: More restricted specificity than pepsin A, but shows preferential cleavage at Tyr bonds. High activity on hemoglobin. References:

Ryle, A. P. The porcine pepsins and pepsinogens. Methods Enzymol. 19 (1970) 316–336

Tang, J. Gastricsin and pepsin. Methods Enzymol. 19 (1970) 406–421

Foltmann, B. Gastric proteinases—structure, function, evolution and mechanism of action. Essays Biochem. 17 (1981) 52–84.

Foltmann, B. and Jensen, A. L. Human progastricsin—analysis of intermediates during activation into gastricsin and determination of the amino-acid sequence of the propart. Eur. J. Biochem. 128 (1982) 63–70.

Martin, P., Trieu-Cuot, P., Collin, J.-C. and Ribadeau Dumas, B. Purification and characterization of bovine gastricsin. Eur. J. Biochem. 122 (1982) 31–39.

Reid, W. A., Vongsorasak, L., Svasti, J., Valler, M. J. and Kay J. Identification of the acid proteinase in human seminal fluid as a gastric sin originating in the prostate. Cell Tissue Res. 236 (1984) 597–600.

Hayano, T., Sogawa, K., Ichihara, Y., Fujii-Kuriyama, Y. and Takahasi, K. Primary structure of human pepsinogen C gene. J. Biol. Chem. 263 (1988) 1382–1385.

EC 3.4.23.4. chymosin: Reaction: Broad specificity similar to that of pepsin A. Clots milk by cleavage of a single Ser-Phe105Met-Ala bond in—chain of casein. References:

Foltmann, B. A review of prorennin and rennin. C. R. Trav. Lab. Carlsberg (1966) 143–231.

Harris, T. J. R., Lowe, P. A., Lyons, A., Thomas, P. G., Eaton, M. A. W., Millican, T. A., Patel, T. P., Bose, C. C., Carey, N. H. and Doel, M. T. Molecular cloning and nucleotide sequence of cDNA coding for calf preprochymosin. Nucleic Acids Res. 10 (1982) 2177–2187.

Visser, S., Slangen, C. J. and van Rooijen, P. J. Peptide substrates for chymosin (rennin). Interaction sites in k-casein-related sequences located outside the (103–108)-hexapeptide region that fits into the enzyme's active-site cleft. Biochem. J. 244 (1987) 553–558.

EC 3.4.23.5, cathepsin D: Reaction: Specificity similar to, but narrower than that of pepsin A. Does not cleave the Gln4-His bond in B chain of insulin. References:

Barrett, A. J. Cathepsin D and other carboxyl proteinases. In Proteinases in Mammalian Cells and Tissues (Barrett, A. J., ed.) p. 209–248 (1977) Elsevier/North-Holland, Amsterdam and London.

Takahashi, T. and Tang, J. Cathepsin D from porcine and bovine spleen. Methods Enzymol. 80 (1981) 565–581.

Faust, P. L., Kornfeld, S. and Chirgwin, J. M. Cloning and sequence analysis of cDNA for human cathepsin D. Proc. Natl Acad. Sci. USA 82 (1985) 4910–4914.

Conner, G. E. Isolation of procathepsin D from mature cathepsin D by pepstatin affinity chromatography. Autocatalytic proteolysis of the zymogen form of the enzyme. Biochem. J. 263 (1989) 601–604.

EC 3.4.23.12, nepenthesin: Reaction: Similar to pepsin, but also cleaves on either side of Asp and at LysArg References:

Amagase, S., Nakayama, S. and Tsugita, A. Acid protease in Nepenthes. II. Study on the specificty of nepenthesin. J. Biochem. (Tokyo) 66 (1969) 431–439.

Garg, G. K. and Virupaksha, T. K. Acid protease from germinated sorghum. 2. Substrate specificity with synthetic peptides and ribonuclease A. Eur. J. Biochem. 17 (1970) 4–12.

Shinano, S. and Fukushima, K. Studies on lotus seed protease. Part III. Some physicochemical and enzymic properties. Agric. Biol. Chem. 35 (1971) 1488–1494.

Amagase, S. Digestive enzymes in insectivorous plants. III. Acid proteases in the genus *Nepenthes* and *Drosera peltata*. J. Biochem. (Tokyo) 72 (1972) 73–81.

Takahashi, K., Chang, W-J. and Ko, J-S. Specific inhibition of acid proteases from brain, kidney, skeletal muscle, and insectivorous plants by diazoacetyl-DL-norleucine methyl ester and by pepstatin. J.Biochem. (Tokyo) 76 (1974) 897–899.

Tökés, Z. A., Woon, W. C. and Chambers, S. M. Digestive enzymes secreted by the carnivorous plant *Nepenthes macferlani L. Planta* 119 (1974) 39–46.

EC 3.4.23.15, renin: Reaction: Cleavage of Leu bond in angiotensinogen to generate angiotensin I. References:

Inagami, T. and Murakami, K. Pure renin. Isolation from hog kidney and characterization. J. Biol. Chem. 252 (1977) 2978–2983.

Slater, E. E. Renin. Methods Enzymol. 80 (1981) 427–442.

Inagami, T. Structure and function of renin. J. Hypertension 7 (Suppl. 2) (1989) S3–S8.

Sielecki, A. R., Hayakawa, K., Fujinaga, M., Murphy, M. E. P., Fraser, M., Muir, A. K., Carilli, C. T., Lewicki, J. A., Baxter, J. D. and James, M. N. G. Structure of recombinant human renin, a target for cardiovascular-active drugs, at 2.5 Å resolution. Science 243 (1989) 1346–1351.

EC 3.4.23.16, HIV-1 retropepsin: Reaction: Specific for a P1 residue that is hydrophobic, and P1' variable, but often Pro. References:

Kuo, L. C. and Shafer, J. A. (eds) Retroviral Proteases. Methods Enzymol. 241 (1994) 1–431.

Dunn, B. M. Human immunodeficiency virus 1 retropepsin. In: Handbook of Proteolytic Enzymes (Barrett, A. J., Rawlings, N. D. and Woessner, J. F. eds), pp. 919–928 (1998) Academic Press, London.

EC 3.4.23.17, pro-opiomelanocortin converting enzyme: Reaction: Cleavage at paired basic residues in certain prohormones, either between them, or on the carboxyl side. References:

Loh, Y. P., Parish, D. C. and Tuteja, R. Purification and characterization of a paired basic residue-specific pro-opiomelanocortin converting enzyme from bovine pituitary intermediate lobe secretory vesicles. J. Biol. Chem. 260 (1985) 7194–7205.

Loh, Y. P. Kinetic studies on the processing of human b-lipotropin by bovine pituitary intermediate lobe pro-opiomelanocortin-converting enzyme. J. Biol. Chem. 261 (1986) 11949–11955.

Estivariz, F. E., Birch, N. P. and Loh, Y. P. Generation of Lys-g3-melanotropin from pro-opiomelanocortin1-77 by a bovine intermediate lobe secretory vesicle membrane-associated aspartic protease and purified pro-opiomelanocortin converting enzyme. J. Biol. Chem. 264 (1989) 17796–17801.

EC 3.4.23.18, aspergillopepsin I: Reaction: Hydrolysis of proteins with broad specificity. Generally favours hydrophobic residues in P1 and P1, but also accepts Lys in P1, which leads to activation of trypsinogen Does not clot milk. References:

Kovaleva, G. G., Shimanskaya, M. P. and Stepanov, V. M. The site of diazoacetyl inhibitor attachment to acid proteinase of *Aspergillus awamori*—an analog of penicillopepsin and pepsin. Biochem. Biophys. Res. Commun. 49 (1972) 1075–1082.

Morihara, K. and Oka, T. Comparative specificity of microbial acid proteinases for synthetic peptides. III. Relationship with their trypsinogen activating ability. Arch. Biochem. Biophys. 157 (1973) 561–572.

Davidson, R., Gertler, A. and Hofmann, T. *Aspergillus oryzae* acid proteinase. Purification and properties, and formation of p-chymotrypsin. Biochem. J. 147 (1975) 45–53.

Chang, W.-J., Horiuchi, S., Takahashi, K., Yamasaki, M. and Yamada, Y. The structure and function of acid proteases. VI. Effects of acid protease-specific inhibitors on the acid proteases from *Aspergillus niger* var. macrosporus. J. Biochem. (Tokyo) 80 (1976) 975–981.

Tanaka, N., Takeuchi, M. and Ichishima, E. Purification of an acid proteinase from *Aspergillus saitoi* and determination of peptide bond specificity. Biochim. Biophys. Acta 485 (1977) 406–416.

Ostoslavskaya, V. I., Kotlova, E. K., Stepanov, V. M., Rudenskaya, G. H., Baratova, L. A. and Belyanova, L. P. Aspergillopepsin F-A carboxylic proteinase from *Aspergillus foetidus*. Bioorg. Khim. 5 (1976) 595–603.

Panneerselvam, M. and Dhar, S. C. Studies on the peptide bond specificity and the essential groups of an acid proteinase from *Aspergillus fumigatus*. Ital. J. Biochem. (1981) 207–216.

Ostoslavskaya, V. I., Revina, L. P., Kotlova, E. K., Surova, I. A., Levin, E. D., Timokhima, E. A. and Stepanov, V. M. The primary structure of aspergillopepsin A, aspartic proteinase from *Aspergillus awamori*. IV. Amino acid sequence of the enzyme. Bioorg. Khim. 12 (1986) 1030–1047.

Yagi, F., Fan, J., Tadera, K. and Kobayashi, A. Purification and characterization of carboxylproteinase from *Aspergillus kawachii*. Agric. Biol. Chem. 50 (1986) 1029–1033.

Majima, E., Oda, K., Murao, S. and Ichishima, E. Comparative study on the specificities of several fungal aspartic and acidic proteinases towards the tetradecapeptide of a renin substrate. Agric. Biol. Chem. 52 (1988) 787–793.

EC 3.4.23.19, aspergillopepsin II: Reaction: Preferential cleavage in B chain of insulin: Asn3Gin, Gly13Ala, Tyr26Thr. References:

Chang, W.-J., Horiuchi, S., Takahashi, K., Yamasaki, M. and Yamada, Y. The structure and function of acid proteases. VI. Effects of acid protease-specific inhibitors on the acid proteases from *Aspergillus niger* var. macrosporus. J. Biochem. (Tokyo) 80 (1976) 975–981.

Iio, K. and Yamasaki, M. Specificity of acid proteinase A from *Aspergillus niger* var. macrosporus towards B-chain of performic acid oxidized bovine insulin. Biochim. Biophys. Acta 429 (1976) 912–924.

EC 3.4.23.20, penicillopepsin: Reaction: Hydrolysis of proteins with broad specificity similar to that of pepsin A, preferring hydrophobic residues at P1 and P1', but also cleaving Gly20Glu in the B chain of insulin. Clots milk, and activates trypsinogen. References:

Mains, G., Takahashi, M., Sodek, J. and Hofmann, T. The specificity of penicillopepsin. Can. J. Biochem. 49 (1971) 1134–1149.

Zevaco, C., Hermier, J. and Gripon, J.-C. Le système protéolytique de Penicillium roqueforti. II—Purification et propriétés de la protéase acide. Biochimie 55 (1973) 1353–1360.

Emi, S., Myers, D. V. and Iacobucci, G. A. Purification and properties of the thermostable acid protease of *Penicillium duponti*. Biochemistry 15 (1976) 842–848.

Hofmann, T. Penicillopepsin. Methods Enzymol. 45 (1976) 434–450.

Hsu, I.-N., Delbaere, L. T. J., James, M. N. G. and Hofmann, T. Penicillopepsin from *Penicillium janthinellum* crystal structure at 2.8 Å and sequence homology with porcine pepsin. Nature 266 (1977) 140–144.

EC 3.4.23.21, rhizopuspepsin: Reaction: Hydrolysis of proteins with broad specificity similar to that of pepsin A, preferring hydrophobic residues at P1 and P1'. Clots milk and activates trypsinogen. Does not cleave Gln4-His, but does cleave His10Leu and Val12Glu in B chain of insulin. References:

Tsuru, D., Hattori, A., Tsuji, H., Yamamoto, T. and Fukumoto, J. Studies on mold proteases. Part II. Substrate specificity of acid protease of *Rhizopus chinensis*. Agric. Biol. Chem. 33 (1969) 1419–1426.

Kurono, Y., Chidimatsu, M., Horikoshi, K. and Ikeda, Y. Isolation of a protease from a *Rhizopus* product. Agric. Biol. Chem. 35 (1971) 1668–1675.

Ohtsuru, M., Tang, J. and Delaney, R. Purification and characterization of rhizopuspesin isozymes from a liquid culture of *Rhizopus chinensis*. Int. J. Biochem. 14 (1982) 925–932.

Suguna, K., Padlan, E. A., Smith, C. W., Carlson, W. D. and Davies, D. R. Binding of a reduced peptide inhibitor to the aspartic proteinase from *Rhizopus chinesis*: implications for a mechanism of action. Proc. Natl Acad. Sci. USA 84 (1987) 7009–7013.

EC 3.4.23.22, endothiapepsin: Reaction: Hydrolysis of proteins with specificity similar to that of pepsin A; prefers hydrophobic residues at P1 and P1', but does not cleave Ala14-Leu in the B chain of insulin or Z-Glu-Tyr. Clots milk. References:

Whitaker, J. R. Protease of *Endothia parasitica*. Methods Enzymol. 19 (1970) 436–445.

Williams, D. C., Whitaker, J. R. and Caldwell, P. V. Hydrolysis of peptide bonds of the oxidized B-chain of insulin by *Endothia parasitica* protease. Arch. Biochem. Biophys. 149 (1972) 52–61.

Barkholt, V. Amino acid sequence of endothiapepsin. Complete primary structure of the aspartic protease from *Endothia parasitica*. Eur. J. Biochem. 167 (1987) 327–338.

Cooper, J., Foundling, S., Hemmings, A., Blundell, T., Jones, D. M., Hallett, A. and Szelke, M. The structure of a synthetic pepsin inhibitor complexed with endothiapepsin. Eur. J. Biochem. 169 (1987) 215–221.

EC 3.4.23.23, mucorpepsin: Reaction: Hydrolysis of proteins, favouring hydrophobic residues at P1 and P1'. Clots milk. Does not accept Lys at P1, and hence does not activate trypsinogen. References:

Arima, K., Yu, J. and Iwasaki, S. Milk-clotting enzyme from *Mucor pusillus* var. lindt. Methods Enzymol. 19 (1970) 446–459.

Ottesen, M. and Rickert, W. The acid protease of Mucor miehei. Methods Enzymol. 19 (1970) 459–460.

Sternberg, M. Bond specificity, active site and milk doting mechanism of the *Mucor miehei* protease. Biochim. Biophys. Acta 285 (1972) 383–392.

Oka, T., Ishino, K., Tsuzuki, H., Morihara, K. and Arima, K. On the specificity of a rennin-like enzyme from *Mucor pusillus*. Agric. Biol. Chem. 37 (1973) 1177–1184.

Baudy, M., Foundling, S., Pavlik, M., Blundell, T. and Kostka, V. Protein chemical characterization of *Mucor pusillus* aspartic proteinase. Amino acid sequence homology with the other aspartic proteinases, disulfide bond arrangement and site of carbohydrate attachment. FEBS Lett. 235 (1988) 271–274.

EC 3.4.23.24, candidapepsin: Reaction: Preferential cleavage at the carboxyl of hydrophobic amino acids, but fails to cleave Leu15-Tyr, Tyr16-Leu and Phe24-Phe of insulin B chain. Activates trypsinogen, and degrades keratin. References:

Remold, H., Fasold, H. and Staib, F. Purification and characterization of a proteolytic enzyme from *Candida albicans*. Biochim. Biophys. Acta 167 (1968) 399–406.

Rüchel, R. Properties of a purified proteinase from the yeast *Candida albicans*. Biochim. Biophys. Acta 659 (1981) 99–113.

Negi, M., Tsuboi, R., Matsui, T. and Ogawa, H. Isolation and characterization of proteinase from *Candida albicans* substrate specificity. J. Invest. Dermatol. 83 (1984) 32–36.

Lott, T. J., Page, L. S., Boiron, P., Benson, J. and Reiss, E. Nucleotide sequence of the *Candida albicans* aspartyl proteinase gene. Nucleic Acids Res. 17 (1989) 1779 only.

EC 3.4.23.25, saccharopepsin: Reaction: Hydrolysis of proteins with broad specificity for peptide bonds. Cleaves -Leu-LeuVal-Tyr-bond in a synthetic substrate. Does not act on esters of Tyr or Arg. References:

Hata, T., Hayashi, R. and Dot, E. Purification of yeast proteinases. Part III. Isolation and physicochemical properties of yeast proteinase A and C. Agric. Biol. Chem. 31 (1967) 357–367.

Meussdoerffer, F., Tortora, P. and Holzer, H. Purification and properties of proteinase A from yeast. J. Biol. Chem. 255 (1980) 12087–12093.

Ammerer, G., Hunter, C. P., Rothman, J. H., Saari, G. C., Valls, L. A. and Stevens, T. H. PEP4 gene of *Saccharomyces cerevisiae* encodes proteinase A, a vacuolar enzyme required for processing of vacuolar precursors. Mol. Cell. Biol. 6 (1987) 2490–2499.

EC 3.4.23.26, rhodotorulapepsin: Reaction: Specificity similar to that of pepsin A. Cleaves Z-LysAla-Ala-Ala and activates trypsinogen. References:

Sawada, J. Studies on the acid-protease of *Paecilomyces varioti* Bainier TPR-220. Part I. Crystallization of the acid-protease of *Paecilomyces varioti* Bainier TPR-220. Agric. Biol. Chem. 27 (1963) 677–683.

Sawada, J. The acid-protease of *Paecilomyces varioti*. III. The specificity of the crystalline acid-protease on synthetic substrates. Agric. Biol. Chem. 28 (1964) 869–875.

Kamada, M., Oda, K. and Murao, S. The purification of the extracellular acid protease of *Rhodotorula glutinis* K-24 and its general properties. Agric. Biol. Chem. 36 (1972) 1095–1101.

Murao, S., Funakoshi, S. and Oda, K. Purification, crystallization and some enzymatic properties of acid protease of *Cladosporium* sp. No. 45-2. Agric. Biol. Chem. 36 (1972) 1327–1333.

Oda, K., Kamada, M. and Murao, S. Some physicochemical properties and substrate specificity of acid protease of *Rhodotorula glutinis* K-24. Agric. Biol. Chem. 36 (1972) 1103–1108.

Oda, K., Funakoshi, S. and Murao, S. Some physicochemical properties and substrate specificity of acid protease isolated from *Cladosporium* sp. No. 45-2. Agric. Biol. Chem. 37 (1973)1723–1729.

Takahashi, K. and Chang, W.-J. The structure and function of acid proteases. V. Comparative studies on the specific inhibition of acid proteases by diazoacetyl-DL-norleucine methyl ester, 1,2-epoxy-3-(p-nitrophenoxy)propane and pepstatin. J. Biochem. (Tokyo) 80 (1976) 497–506.

Majima, E., Oda, K., Murao, S. and Ichishima, E. Comparative study on the specificities of several fungal aspartic and acidic proteinases towards the tetradecapeptide of a renin substrate. Agric. Biol. Chem. 52 (1988) 787–794.

EC 3.4.23.27, physaropepsin: Reaction: Milk clotting activity. Preferential cleavage of Gly8Ser in B chain of insulin most rapidly, followed by Leu11Val, Cys(SO3H) 19Gly and Phe24Phe. No action on Ac-Phe-Tyr(I)2. References:

Henney, H. R. and Tavana, G. Purification and some properties of an intracellular acid (carboxyl) proteinase from differentiating haploid cells of *Physarum flavicomum*. Exp. Mycol. 6 (1982) 161–170.

Murakami-Murofushi, K., Hiratsuka, A. and Ohta, J. A novel acid protease from haploid amoebae of *Physarum polycephalum*, and its changes during mating and subsequent differentiation into diploid plasmodia. Cell Struct. Funct. 9 (1984) 311–315.

North, M. J. and Whyte, A. Purification and characterization of two acid proteinases from *Dictyostelium discoideum*. J. Gen. Microbiol. 130 (1984) 123–134.

Murakami-Murofushi, K., Takahashi, T., Minowa, Y., Iino, S., Takeuchi, T., Kitagaki-Ogawa, H., Murofushi, H. and Takahashi, K. Purification and characterization of a novel intracellular acid proteinase from the plasmodia of a true slime mold, *Physarum polycephalum*. J. Biol. Chem. 265 (1990) 19898–19903.

EC 3.4.23.28, acrocylindropepsin: Reaction: Preference for hydrophobic residues at P1 and P1'. Action on the B chain of insulin is generally similar to that of pepsin A, but it also cleaves Leu6Cys(SO3H), Glu21Arg and Asn3Gln, although not Gln3-His. References:

Uchino, F., Kurono, Y. and Doi, S. Purification and some properties of crystalline acid protease from *Acrocylindrium* sp. Agric. Biol. Chem. 31 (1967) 428–434.

Ichihara, S. and Uchino, F. The specificity of acid proteinase from *Acrocylindrium*. Agric. Biol. Chem. 39 (1975) 423–428.

Takahashi, K. and Chang, W.-J. The structure and function of acid proteases. V. Comparative studies on the specific inhibition of acid proteases by diazoacetyl-DL-norleucine methyl ester, 1,2-epoxy-3-(p-nitrophenoxy)propane and pepstatin. J. Biochem. (Tokyo) 80 (1976) 497–506.

EC 3.4.23.29, polyporopepsin: Reaction: Milk clotting activity, broad specificity, but fails to cleave Leu15-Tyr or Tyr16-Leu of insulin B chain. References:

Kobayashi, H., Kusakabe, I. and Murakami, K. Substrate specificity of a carboxyl proteinase from *Irpex lacteus*. Agric. Biol. Chem. 47 (1983) 1921–1923.

Kobayashi, H., Sekibata, S., Shibuya, H., Yoshida, S., Kusakabe, I. and Murakami, K. Cloning and sequence analysis of cDNA for *Irpex lacteus* aspartic proteinase. Agric. Biol. Chem. 53 (1989) 1927–1933.

EC 3.4.23.30, pycnoporopepsin: Reaction: Similar to pepsin A, but narrower, cleaving only three bonds in the B chain of insulin: Ala14Leu, Tyr16Leu, and Phe24Phe. References:

Tomoda, K. and Shimazono, H. Acidprotease produced by *Trametes sanguinea* a wood-destroying fungus. Part I. Purification and crystallization of the enzyme. Agric. Biol. Chem. 28 (1964) 770–773.

Tsuru, D., Hattori, A., Tsuji, H., Yamamoto, T. and Fukumoto, J. Studies on mold proteases. Part II. Substrate specificity of acid protease of *Rhizopus chinensis*. Agric. Biol. Chem. 33 (1969) 1419–1426.

Ichishima, E., Kumagai, H. and Tomoda, K. Substrate specificity of carboxyl proteinase from *Pycnoporus coccineus*, a wood-deteriorating fungus. Curr. Microbiol. 3 (1980) 333–337.

EC 3.4.23.31, scytalidopepsin A: Reaction: Hydrolysis of proteins with specificity similar to that of pepsin A, but also cleaves Cys(SO3H)7Gly and Leu17Val in the B chain of insulin. References:

Oda, K. and Murao, S. Purification and some enzymatic properties of acid protease A and B of *Scytalidium lignicolum* ATCC 24568. Agric. Biol. Chem. 38 (1974) 2435–2444.

Oda, K. and Murao, S. Action of *Scytalidium lignicolum* acid proteases on insulin B-chain. Agric. Biol. Chem. 40 (1976) 1221–1225.

Oda, K., Torishima, H. and Murao, S. Purification and characterization of acid proteinase C of *Scytalidium lignicolum* ATCC 24568. Agric. Biol. Chem. 50 (1986) 651–658.

EC 3.4.23.32, scytalidopepsin B: Reaction: Hydrolysis of proteins with broad specificity, cleaving Phe24Phe, but not Leu15-Tyr and Phe25-Tyr in the B chain of insulin. References:

Terashita, T., Oda, K., Kono, M. and Murao, S. *Streptomyces* pepsin inhibitor-insensitive carboxyl proteinase from *Lentinus edodes*. Agric. Biol. Chem. 45 (1981) 1937–1943.

Maita, T., Nagata, S., Matsuda, G., Maruta, S., Oda, K., Murao, S. and Tsuru, D. Complete amino acid sequence of *Scytalidium lignicolum* acid protease B. J. Biochem. (Tokyo) 95 (1984) 465–473.

Terashita, T., Oda, K., Kono, M. and Murao, S. *Streptomyces* pepsin inhibitor-insensitive carboxyl proteinase from *Ganoderma lucidum*. Agric. Biol. Chem. 48 (1984) 1029–1035.

Kobayashi, H., Kusakabe, I. and Murakami, K. Purification and characterization of a pepstatin-insensitive carboxyl proteinase from *Polyporus tulipiferae* (*Irpex lacteus*). Agric. Biol. Chem. 49 (1985) 2393–2397.

Tsuru, D., Shimada, S., Maruta, S., Yoshimoto, T., Oda, K., Murao, S., Miyata, T. and Iwanaga, S. Isolation and amino acid sequence of a peptide containing an epoxide-reactive residue from the thermolysin-digest of *Scytalidium lignicolum* acid protease B. J. Biochem. (Tokyo) 99 (1986) 1537–1539.

EC 3.4.23.33, xanthomonapepsin: Reaction: Cleavage of casein. References:

Oda, K., Nakazima, T., Terashita, T., Suzuki, K. and Murao, S. Purification and properties of an S-PI(pepstatin Ac)-insensitive carboxyl proteinase from a *Xanthomonas* sp. bacterium. Agric. Biol. Chem. 51 (1987) 3073–3080.

EC 3.4.23.34, cathepsin E: Reaction: Similar to cathepsin D, but slightly broader specificity. References:

Lapresle, C., Puizdar, V., Porchon-Bertolotto, C., Joukoff, E. and Turk, V. Structural differences between rabbit cathepsin E and cathepsin D. Biol. Chem. Hoppe-Seyler 367 (1986) 523–526.

Yonezawa, S., Fujii, K., Maejima, Y., Tamoto, K., Mori, Y. and Muto, N. Further studies on rat cathepsin E: subcellular localization and existence of the active subunit form. Arch. Biochem. Biophys. 267 (1988) 176–183.

Jupp, R. A., Richards, A. D., Kay, J., Dunn, B. M., Wyckoff, J. B., Samloff, I. M. and Yamamoto, K. Identification of the aspartic proteinases from human erythrocyte membranes and gastric mucosa (slow-moving proteinase) as catalytically equivalent to cathepsin E. Biochem. J. 254 (1988) 895–898.

Azuma, T., Pals, G., Mohandas, T. K., Couvreur, J. M. and Taggart, R. T. Human gastric cathepsin E. Predicted sequence, localization to chromosome 1, and sequence homology with other aspartic proteinases. J. Biol. Chem. 264 (1989) 16748–16753.

EC 3.4.23.35, barrierpepsin: Reaction: Selective cleavage of -Leu6Lys- bond in the pheromone a-mating factor. References:

Mackay, V. L., Welch, S. K., Insley, M. Y., Manney, T. R., Holly, J., Saari, G. C. and Parker, M. L. The *Saccharomyces cerevisiae* BAR1 gene encodes an exported protein with homology to pepsin. Proc. Natl. Acad. Sci. USA 85 (1988) 55–59.

Mackay, V. L., Armstrong, J., Yip, C., Welch, S., Walker, K., Osborn, S., Sheppard, P. and Forstrom, J. Characterization of the bar proteinase, an extracellular enzyme from the yeast *Saccharomyces cerevisiae*. Adv. Exp. Med. Biol. 306 (1991) 161–172.

EC 3.4.23.36, signal peptidase II: Reaction: Release of signal peptides from bacterial membrane prolipoproteins including murein prolipoprotein. Hydrolyses -Xaa-Xbb-Xcc (S,diacylglyceryl)Cys-, in which Xaa is hydrophobic (preferably Leu), and Xbb (Ala or Ser) and Xcc (Gly or Ala) have small, neutral sidechains. References:

Dev, I. K. and Ray, P. H. Signal peptidases and signal peptide hydrolases. J. Bioenerg. Biomembr. 22 (1990) 271–290.

Zhao, X.-J. and Wu, H. C. Nucleotide sequence of the *Staphylococcus aureus* signal peptidase II (lsp) gene. FEBS Lett. 299 (1992) 80–84.

Sankaran, K. and Wu, H. C. Bacterial prolipoprotein signal peptidase. Methods Enzymol. 248 (1995)169–180.

EC 3.4.23.37, pseudomonapepsin: Reaction: Hydrolysis of the 13 chain of insulin at -Glu13Ala-, -Leu15Tyr- and -Phe25Tyr-, and angiotensin I at -Tyr4Ile-. A good synthetic substrate is Lys-Pro-Ile-Glu-PhePhe(NO2)-Arg-Leu. References:

Oda, K., Sugitani, M., Fukuhara, K. and Murao, S. Purification and properties of a pepstatin-insensitive carboxyl proteinase from a Gram-negative bacterium. Biochim. Biophys. Acta 923 (1987) 463–469.

Oda, K., Fukuda, Y., Murao, S., Uchida, K. and Kainosho, M. A novel proteinase inhibitor, tyrostatin, inhibiting some pepstatin-insensitive carboxyl proteinases. Agric. Biol. Chem. 53 (1989) 405–415.

Oda, K. and Murao, S. Pepstatin-insensitive carboxyl proteinases. In Structure and Function of Aspartic Proteinases (Dunn, B. M., ed.), pp. 185–201 (1991) Plenum Press, New York.

Oda, K., Nakatani, H. and Dunn, B. M. Substrate specificity and kinetic properties of pepstatin-insensitive carboxyl proteinase from *Pseudomonas* sp. No. 101. Biochim. Biophys. Acta 1120 (1992) 208–214.

EC 3.4.23.38, plasmepsin I: Reaction: Hydrolysis of the -Phe33Leu- bond in the a-chain of hemoglobin, leading to denaturation of the molecule. References:

Goldberg, D. E., Slater, A. F. G., Beavis, R., Chait, B., Cerami, A. and Henderson, G. B. Hemoglobin degradation in the human malaria pathogen *Plasmodium falciparum:* a catabolic pathway initiated by a specific aspartic protease. J. Exp. Med. 173 (1991) 961–969.

Francis, S. E., Gluzman, I. Y., Oksman, A., Knickerbocker, A., Mueller, R., Bryant, M. L., Sherman, D. R., Russell, D. G. and Goldberg, D. E. Molecular characterization and inhibition of a *Plasmodium falciparum* aspartic hemoglobinase. EMBO J. 13 (1994) 306–317.

Gluzman, I. Y., Francis, S. E., Oksman, A., Smith, C. E., Duffin, K. L. and Goldberg, D. E. Order and specificity of the *Plasmodium falciparum* hemoglobin degradation pathway. J. Clin. Invest. 93 (1994) 1602–1608.

EC 3.4.23.39, plasmepsin II: Reaction: Hydrolysis of the bonds linking certain hydrophobic residues in hemoglobin or globin. Also cleaves the small molecule substrates such as Ala-Leu-Glu-Arg-Thr-PhePhe(NO2)-Ser-Phe-Pro-Thr. References:

Dame, J. B., Reddy, G. R., Yowell, C. A., Dunn, B. M., Kay, J. and Berry, C. Sequence, expression and modelled structure of an aspartic proteinase from the human malaria parasite *Plasmodium falciparum*. Mol. Biochem. Parasitol. 64 (1994) 177–190.

Gluzman, I. Y., Francis, S. E., Oksman, A., Smith, C. E., Duffin, K. L. and Goldberg, D. E. Order and specificity of the *Plasmodium falciparum* hemoglobin degradation pathway. J. Clin. Invest. 93 (1994) 1602–1608.

Hill, J., Tyas, L., Phylip, L. H., Kay, J., Dunn, B. M. and Berry, C. High level expression and characterisation of plasmepsin II, an aspartic proteinase from *Plasmodium falciparum*. FEBS Lett. 352 (1994) 155–158.

EC 3.4.23.40, phytepsin: Reaction: Prefers hydrophobic residues Phe, Val, Ile, Leu, and Ala at P1 and P1', but also cleaves -Phe, Asp- and -AspAsp- bonds in 2S albumin from plant seeds. References:

Runeberg-Roos, P., Törmäkangas, K. and Östman, A. Primary structure of a barley-grain aspartic proteinase. A plant aspartic proteinase resembling mammalian cathepsin D. Eur. J. Biochem. 202 (1991) 1021–1027.

Kervinen, J., Sarkkinen, P., Kalkkinen, N., Mikola, L. and Saarma, M. Hydrolytic specificity of the barley grain aspartic proteinase. Phytochemistry 32 (1993) 799–803.

Asakura, T., Watanabe, H., Abe, K. and Arai, S. Rice aspartic proteinase, oryzasin, expressed during seed ripening and germination, has a gene organization distinct from those of animal and microbial aspartic proteinases. Eur. J. Biochem. 232 (1995) 77–83.

Kervinen, J., Törmäkangas, K., Runeberg-Roos, P., Guruparasad, K., Blundell, T. and Teeri, T. H. Structure and possible function of aspartic proteinases in barley and other plants. Adv. Exp. Med. Biol. 362 (1995) 241–254.

EC 3.4.23.41, yapsin 1: Reaction: Hydrolyses various precursor proteins with Arg or Lys in P1, and commonly Arg or Lys also in P2. The P3 amino acid is usually non-polar, but otherwise additional basic amino acids are favorable in both non-prime and prime positions. References:

Cawley, N. X., Chen, H. C., Beinfeld, M. C. and Loh, Y. P. Specificity and kinetic studies on the cleavage of various prohormone mono- and paired-basic residue sites by yeast aspartic protease 3. J. Biol. Chem. 271 (1996) 4168–4176.

Fuller, R. S. Yapsin 2. In: Handbook of Proteolytic Enzymes, (Barrett, A. J., Rawlings, N. D. and Woessner, J. F. eds), pp. 908–909 (1998) Academic Press, London.

Olsen, V., Guruprasad, K., Cawley, N. X., Chen, H. C., Blundell, T. L. and Loh, Y. P. Cleavage efficiency of the novel aspartic protease yapsin 1 (Yap3p) enhanced for substrates with arginine residues flanking the P1 site: correlation with electronegative active-site pockets predicted by molecular modeling. Biochemistry 37 (1998) 2768–2777.

EC 3.4.23.42, thermopsin: Reaction: Similar in specificity to pepsin A preferring bulky hydrophobic amino acids in P1 and P1'. References: Lin, X. and Tang, J. Thermopsin. Methods Enzymol. 248 (1995) 156–168.

The Low-Barrier Hydrogen Bond:

Piana & Carloni[5] performed ab initio molecular dynamics simulations on HIV-1 protease. Their investigation focused on the conformational flexibility of the active site carboxyls, Asp 25 and Asp 25'. They found that the mono-protonated form of HIV-1 protease is the most stable. This stability is due to the presence of a low-barrier hydrogen bond between the Oδ1 atoms. See FIG. 1.

The hydrogen bond compensates for the negative charge repulsion of the two oxygen atoms and holds them within an interatomic distance of 2.5±0.1 Å. Moreover, the low-barrier hydrogen bond, coupled with peptide dipoles, functions to hold the two carboxyl groups of the active site in a coplanar conformation. A water molecule is trapped between—and hydrogen bonded to—both of the co-planar Oδ2 atoms, as shown in FIG. 1. The resulting symmetrical 10-atom cyclized structure thus provides the scaffold to impart proximity, orientation and nucleophilicity to the water molecule.

There are several dominant characteristics to this low-barrier hydrogen bond:

(1) a high reliance upon matched pKs of the electronegative atoms sharing the hydrogen (2) low fractionation factors when deuterium replaces hydrogen (3) downfield chemical shifts of 18–22 ppm for the hydrogen in proton NMR spectra.

The first characteristic is obviously satisfied with a pairing of two carboxyls. The second characteristic will be discussed in detail below. The third characteristic has never been observed in aspartic proteases until now, presumably because of autolysis encountered with high concentrations of free protease. However, the inhibited complex between HIV-1 protease and pepstatin has been examined by proton NMR, with negative results.[8]

Consistent with that finding are additional ab initio molecular dynamics simulations by Piana et al.[9] showing that in the most stable form of the protease-pepstatin complex both carboxyl groups are protonated and there is no shared low-barrier hydrogen bond. $^{13}$C-NMR spectra of HIV-1 protease specifically labeled in the Asp 25 and Asp 25' carboxyls show a single peak in the free enzyme and two peaks in the pepstatin complex.[8] These observations are consistent with a low-barrier hydrogen bond in the free enzyme that causes both carboxyls to appear ionized, while different electronic environments in the enzyme-substrate complex cause the two protonated carboxyls to express different chemical shifts.[9]

pH Kinetics:

For almost a century it has been thought that two ionizable groups were involved in the enzymatic activity of pepsin, one protonated and one not, with pKs approaching extremes of 4 and 1, respectively. The first ionizable group was obviously a carboxyl. But the second group seemed much too acidic to be a carboxyl. When a phosphoric acid residue was found in porcine pepsin A, it became a candidate for the low pK group, but dephosphorylation had no effect on activity. When both groups were deemed carboxyls, it seemed necessary to propose different environments for them. Thus, one group was attributed to the hydrophobic active site of the enzyme and the other group to peptide substrates. But esterification of carboxyl groups of substrates has no enzymatic effect either, thereby leaving the origin of the low pK maddeningly unresolved for another thirty years.

The response of low-barrier hydrogen bonds to $D_2O$, as described herein, finally solves this 92 year-old mystery and simultaneously provides a means to evaluate the efficacy of potential aspartic protease inhibitors. During hydrolysis of N-trifluroacetyl-L-phenylalanine, Hunkapillar & Richards[10] observed bell-shaped pH profiles which were shifted to the right, but the upper pK profiles shifted to the left, thereby bringing them closer together. Normally, $D_2O$ shifts all pKs to the right about half a unit because of the fractionation factor of $H_3O^+$.[11]

Figures 2A, 2B:
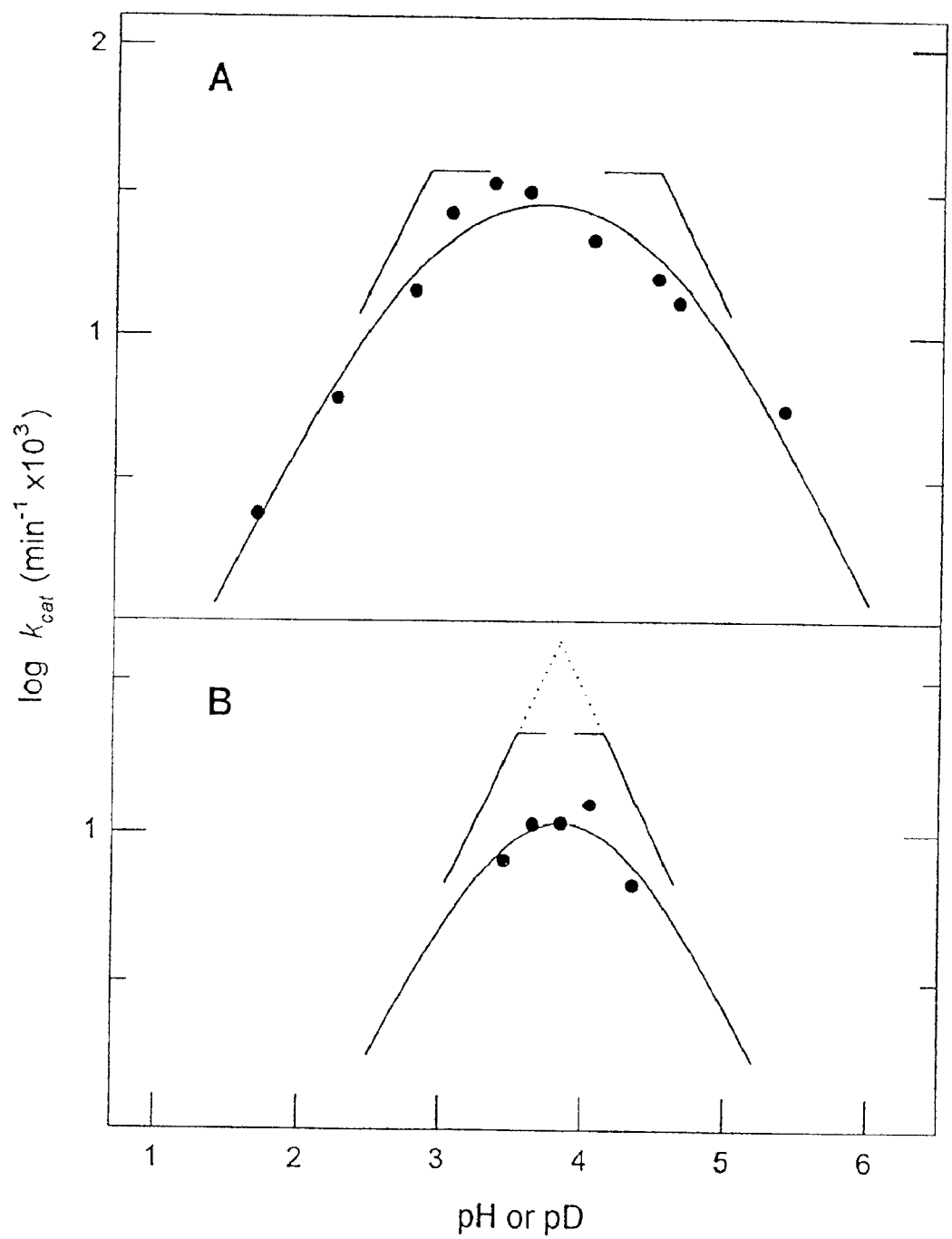
FIG. 2: Kinetics of pepsin acting on N-trifluroacetyl-L-phenylalanine as a function of pH (A) and pD (B). The fitted pH-independent kinetic constants are $k_{cat}=0.038\pm0.006$ min$^{-1}$ in H$_2$O and $k_{cat}=0.022\pm2$ min$^{-1}$ in D$_2$O. The dotted line indicates the range of carboxyl pKs consistent with the fitted line in D$_2$O.

A re-analysis of the pH profiles of $k_{cat}$ from Hunkapillar & Richards is presented in FIGS. 2A and 2B. The fit to the BELL rate equation of data obtained in $H_2O$ converged with pKs of 2.9±0.1 and 4.5±0.1, while those in $D_2O$ converged to the default separation of only 0.6 units, the minimum that is statistically possible. The fitted curve in FIG. 2B is the same for identical pKs of 3.84±0.08 or separated pKs of 3.5 and 4.1—or anything in between. Unknown in 1972, low-barrier hydrogen bonds are now understood to cause opposite shifts in the pKs of the conjugate bases participating in the bond. Both protonation and deprotonation of the low-barrier hydrogen bond complex are made more difficult, which shifts apparent pKs outwards in $H_2O$ but less so in $D_2O$.[7]

By comparing the maximal values of their fitted curves, Hunkapillar & Richards estimated that $^{D2O}k_{cat} \approx 3$. However, the appropriate comparison note between the absolute maxima, but between the pH-independent maxima,[11] represented by the horizontal bars in FIGS. 2A and 2B. This ratio yields $^{D2O}k_{cat}=1.8\pm0.4$ for pKs separated by 0.6 units, and lower values if the fractionation factor is greater than 0.3. Hence, the actual kinetic isotope effect for pepsin hydrolysis of N-trifluroacetyl-L-phenylalanine in $D_2O$ is modest, and most of the effect has a thermodynamic origin: a weakening of the low-barrier hydrogen bond causing a large decrease in enzyme poised for catalysis. The narrowness of pH profiles in $D_2O$ suggests that this pH-dependent step is fully expressed. In contrast, pH profiles of HIV-1 protease show both pKs of $k_{cat}/K_M$ further apart and both shifted to the right in $D_2O$, with only the lower pK expressed in $k_{cat}$ profiles.[12] These contrasts require: (1) that the pH-dependent step being expressed in HIV-1 protease is a different step than that in the pepsin studies; (2) that it comes later in the kinetic mechanism than the loss of the low-barrier hydrogen bond; and (3) that it not be fully expressed in either $k_{cat}$ or $k_{cat}/K_M$, which causes apparent pKs to be shifted outwards even further.

The Kinetic Iso-Mechanism:

The artificial peptide Leu-Ser-Nph-Nle-Ala-Leu-OMe (SEQ. ID. NO: 1) was synthesized as a chromophoric substrate for industrial assays of chymosin used in making cheese, but it turned out to be an excellent substrate for pepsin as well.[13] Values of $k_{cat}$ are pH-independent and orders of magnitude greater than pH-dependent values of earlier synthetic peptide substrates, indicating a difference in rate-limiting reaction segments.

This "fast substrate" also displayed a solvent isotope effect of $^{D2O}k_{cat}=1.51\pm0.02$, coupled to no effect on $k_{cat}/K_M$, thus requiring that an isotopically-sensitive step comes after the first irreversible step (the release of a product) in an isomerization segment of the kinetic mechanism. While not being limited to a particular mode of action, an isomechanism has been formulated to account for the observed kinetics. Specifically, the proposed isomechanism includes a substrate form of enzyme, E, having a proton located on one active-site carboxyl group, and a product form, F, having the proton located on the other carboxyl group. Such an iso step provides a proton transfer that could generate a kinetic isotope effect on $k_{cat}$ but not on $k_{cat}/K_M$.

The case for an isomechanism was confirmed by isotope effects on the slow onset of inhibition by pepstatin. A normal $^{D2O}k=1.25\pm0.09$ occurs when catalysis is in progress. But, a surprising inverse $^{D2O}k=0.69\pm0.09$ is expressed during preincubation experiments with free enzyme.[14] Proton inventories on both are linear, indicating single proton transfers. (This is unlike inventories on substrate capture, see below). Hence, during catalysis the inhibitor binds to an iso form of the enzyme that is different from the form of the enzyme that binds substrate. In preincubations, however, the inhibitor binds to the same form of the enzyme by a two-step process, $E+I \rightleftharpoons EI \rightleftharpoons FI$.

The slow second step has been assigned to the release of a tightly-bound water molecule. But it remained unclear how $D_2O$ could be bound less tightly. The present inventor has determined that the low fractionation factor of a low-barrier hydrogen bond in free aspartic protease, E, versus no low-barrier hydrogen bond in the tightened pepstatin-enzyme complex, FI, provides a clear resolution of this uncertainty: the F form of enzyme is favored in $D_2O$, which accounts for the inverse effect. (The normal effect will be addressed below, after the chemical mechanism.)

Product Inhibition Mechanisms:

In an ordered uni-bi kinetic mechanism, the first product is a non-competitive inhibitor and the second product is a competitive inhibitor; however, if free enzyme isomerizes within an isomechanism, then both appear non-competitive. Accordingly, on the basis of graphical analysis of product inhibition patterns, pepsin was deemed to follow an ordered mechanism with the scissile carboxyl product released first. However, Rebholz[15] re-analyzed the published competitive inhibition patterns using newer regression methods and found that several had small but statistically significant intercept effects, i.e. $K_{is} << K_{ii}$.

TABLE I

Product Inhibition Kinetics of HIV-1 Protease[15]

| Substrate/Product | $K_{is}$ (mM) | $K_{ii}$ (mM) | $^{D2O}K_{is}$ | $^{D2O}K_{ii}$ |
|---|---|---|---|---|
| Ac-Ser-Glu-Asp-Tyr* Phe-Leu-Asp-Gly-$NH_2$ (SEQ. ID. NO: 2) | | | | |
| Phe-Leu-Asp-Gly-$NH_2$ | 12 | 4 | 1.1 ± 0.4 | 3.0 ± 0.9 |
| Ac-Ser-Glu-Asp-Tyr (SEQ. ID. NO: 3) | 3.8 | 12 | 4.2 ± 1.6 | 3.8 ± 1.3 |
| Ac-Ser-Glu-Asp-Tyr* Phe-Leu-Asp-Gly-$NH_2$ (SEQ. ID. NO: 4) | | | | |
| Ac-Arg-Ala-Ser-Glu-Asp-Tyr (SEQ. ID. NO: 5) (pH 6) | 7 | 8 | 4.2 ± 1.6 | 3.8 ± 1.3 |
| Ac-Ser-Glu-Asp-Tyr* Phe-Val-Val-$NH_2$ (SEQ. ID. NO: 6) Ac-Arg-Ala-Ser-Glu-Asp-Tyr (SEQ. ID. NO: 7) | | | | |
| (pH 4.5) | | | 1.2 ± 0.4 | 1.0 ± 0.8 |
| (pH 3.5) | — | 0.23 | | |

Later, in HIV-1 protease kinetic studies, Rodrigues and Meek[16] found unambiguous non-competitive patterns along with inverse solvent isotope effects on some product inhibition constants, as shown in Table I (above).

Figure 3:
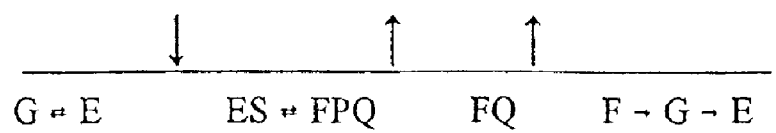
FIG. 3: Line diagram of a two-step iso uni-bi ordered kinetic mechanism. The first iso step, F→G, deprotonation of the carboxyl with the lower pK, is effectively irreversible at the pH optimum and contributes only to $k_{cat}$. The second iso step, G⇌E, is shown as reversible in the beginning of the mechanism as it would appear in $k_{cat}/K_M$, and irreversible at the end of the mechanism, as it would appear in $k_{cat}$.

The scissile amino product Phe-Leu-Asp-Gly-$NH_2$, for example, is non-competitive when $K_{is} > K_{ii}$ and has a large solvent isotope effect on $K_{ii}$. Solvent isotope effects on ligand binding are unexpected because reactant-state fractionation factors of exchangeable protons are usually $\Phi \approx 1.0$.[11] But this $^{D2O}K_{ii}$ arises from solvent perturbations of kinetic turnovers. At saturating concentrations of substrate, inhibitors bind to transient product forms of the enzyme, such as F or FQ in FIG. 3. In $D_2O$, the conversion of F to E is retarded, causing an increase in the concentration of F which in turn enhances inhibitor binding. Better binding generates a lower inhibition constant and appears as a normal isotope effect, i.e. $K_H/K_D > 1$. Hence, this large solvent isotope effect on $K_{ii}$ has a kinetic origin, due to changes in the distribution of product forms of enzyme, and is not an effect on "binding" as such.

Similar results are obtained with the scissile carboxyl products in Table I, only now both inhibition constants show normal solvent isotope effects. The $K_{is}$ term represents binding at low substrate concentration, which means the free enzyme forms are in equilibrium and any solvent isotope effect must have a thermodynamic origin. Therefore, a $K_H/K_D>1$ is consistent with binding being favored in $D_2O$. This means that Ac-Ser-Glu-Asp-Tyr prefers enzyme without a low-barrier hydrogen bond.

Returning to the scissile amino product, its $^{D2O}K_{is} \approx 1$ means that Phe-Leu-Asp-Gly-$NH_2$ shows no such favoritism; it binds equally well with or without a low-barrier hydrogen bond. Why, however, is its $K_{ii}$ so much smaller than $K_{is}$? This apparent paradox is resolved by proposing an additional isomer of free enzyme, G, that lacks a low-barrier hydrogen bond. Because transpeptidation data (see below) show the F form to be di-protonated, the additional form is most likely mono-protonated within the two-step isomechanism shown in FIG. 3. At low substrate concentration, inhibitors bind to G or E, or both, at equilibrium with G favored in $D_2O$; at high substrate concentration, they bind to F and G, which are in steady-state transit with F favored in $D_2O$.

This two-step proposal is strengthened by the remaining inhibition constants in Table I for the alternate scissile carboxyl product, Ac-Arg-Ala-Ser-Glu-Asp-Tyr. At pH 6, the $K_{is}$ and $K_{ii}$ values are similar and both display solvent isotope effects. At pH 4.5, the non-competitive pattern loses its solvent isotope effects. But at pH 3.5, the pattern appears uncompetitive—with a lower $K_{ii}$ than at pH 6. It follows that this product does not bind to the E form with a low-barrier hydrogen bond, but will bind to either G or F, with a strong preference for F (and probably FQ).

The Non-Covalent Transpeptidation Mechanism:

When Tyr-Tyr was produced from Cbz-Glu-Tyr and pepsin, Neumann et al.[17] proposed an amino-enzyme covalent intermediate. But when both ($^3$H)Leu-($^3$H)Leu and ($^{14}$C)Leu-($^{14}$C)Leu were produced from ($^{14}$C)Leu-Tyr-($^3$H)Leu[18]—in an unequal ratio—the construction of a plausible covalent chemical mechanism became difficult.[4] Both acyl- and amino-enzymes seemed necessary but unlikely and the lack of stoichiometry was unsettling.

The kinetic isomechanism present herein provides an alternative pathway for peptide bond synthesis without covalent intermediates. Moreover, the isomechanism accommodates the lack of stoichiometry. A lag is present in the progress curve of an acyl transpeptidation reaction catalyzed by pepsin acting on Leu-Ser-Nph-Nle-Ala-Leu-OMe in the presence of excess Leu-Leu to form Leu-Ser-Nph-Leu-Leu.[19] Most importantly, the lag is tightly coupled to bursts in the progress curves of the proteolytic products, Leu-Ser-Nph and Nle-Ala-Leu-OMe. But, neither lags nor bursts are expected if an acyl covalent intermediate is involved, e.g. Leu-Ser-Nph-enzyme.

That the transpeptidation reaction unequivocally requires an isomechanism was established by the measurement of normal isotope effects with $^{D2O}k \approx 2$ on proteolysis, coupled to an inverse solvent isotope effect of $^{D2O}k = 0.40 \pm 0.09$ on transpeptidation. The lags and bursts mean that, under these conditions, some or all of the scissile carboxyl product, Leu-Ser-Nph, dissociates and must accumulate before a significant amount is joined to Leu-Leu by transpeptidation. Dissociation and rebinding allows for the joining of diverse acyl and amino groups without regard to stoichiometry. The normal isotope effect on turnover, coupled to an inverse effect on transpeptidation, means a step subsequent to Leu-Ser-Nph dissociation is slower in $D_2O$. This is a step beyond the formation of F.

As in the product inhibition studies, $D_2O$ causes the concentration of F to accumulate, so more pepsin can bind Leu-Ser-Nph and catalyze transpeptidation. Evidence that F is the di-protonated form of enzyme comes from transpeptidations catalyzed by penicillopepsin. These reactions display a pH optimum about one unit below the optimum for proteolysis.[20] Under different conditions, one or the other of the proteolytic products may dissociate poorly from F, and thereby dominate transpeptidation from an FQ complex.

For example, pepsin acting on Ala-Ala-Nph-Nph at pH 5.5 generates varying amounts of products, with Ala-Ala-Nph>Nph-Nph-Nph>Ala-Ala-Nph-Nph-Nph>Nph-Nph>Nph>Nph-Nph-Nph-Nph.[21] Moreover, running these transpeptidation reactions in the presence of added free ($^3$1H)Nph failed to produce any labeled products. Obviously, very little scissile amino product Nph dissociates from pepsin and rebinds under these conditions.

Figure 4:
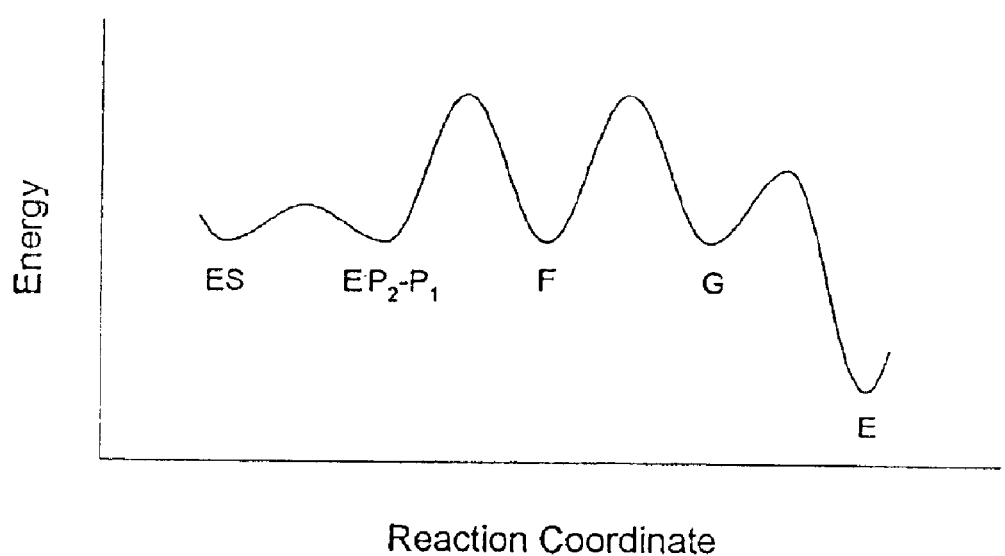
FIG. 4: Activation energy diagram for proteolysis catalyzed by pepsin. Enzyme is saturated with substrate S and the reaction effectively begins with ES. Transpeptidation can occur by rebinding of products P$_1$ and P$_2$ (or an added peptide P', not shown) to enzyme form F. Product complex F(P$_1$)(P$_2$) can regenerate ES (or synthesize EP$_2$-P') coupled to formation of an low-barrier hydrogen bond. Enzyme forms G and E cannot support transpeptidation because the former is kinetically incompetent, i.e. it is short-lived, and the latter is energetically incompetent, i.e. it must lose a low-barrier hydrogen bond.

The non-covalent pathway requires that most of the free energy drop associated with peptide bond hydrolysis takes place in the iso segment and not in the chemical segment. This proviso is needed because sometimes the amount of transpeptidation products formed equals or exceeds proteolytic products, as in the example immediately above. The disparity requires the energy level of FQ to approximate or exceed that of ES, as illustrated in FIG. 4, such that products or peptides binding to F can readily flow back through the chemical segment to form a new peptide bond. A low-barrier hydrogen bond at the end of that flow provides the energy for synthesis.

For example, the formation of a low-barrier hydrogen bond in ketosteroid isomerase has been estimated to contribute over 7 kcal/mol to the stabilization of an intermediate.[22] This is more than enough energy to drive the synthesis of peptide bonds, which have heats of formation of approximately 2 kcal/mole.[23] Moreover, peptide bond hydrolysis in organic solvents has an equilibrium near one (1); therefore, the energetics suggested in FIG. 4 within a hydrophobic active site and coupled to the formation of a low-barrier hydrogen bond are likely.

Solvent Isotope Effects and Proton Inventories:

Traditionally, it has been assumed that the fractionation factors of exchangeable enzyme protons are similar to that of water (with the notable exception of thiols).[11] But this is certainly not the case for a low-barrier hydrogen bond in a reactant state because low-barrier hydrogen bonds are disfavored in $D_2O$ by as much as a factor of two or three.[7] Consequently, substrate capture, which employs free enzyme as its sole reactant state,[24] must express a normal solvent isotope effect of 2 to 3 regardless of the shape of its energy profile so long as a low-barrier hydrogen bond is lost before the first irreversible step.

In short, the fractionation factor for the formation of the low-barrier hydrogen bond in free enzyme, E, relative to solvent, S, is given by:

$$\phi^E = \frac{[E-D]/[E-H]}{[SOD]/[SOH]} = 0.3 - 0.5 \quad (1)$$

The fractionation factor for protonation of one carboxyl group in the G form of free enzyme without a low-barrier hydrogen bond is assumed to be $\Phi^G=1$. Hence, with the E form as the reference reactant-state, the operative factor for $G \rightleftharpoons E \rightarrow (ES)$ is $\Phi^G/\Phi^E=1/(0.3-0.5)=2-3$. With the energy level of the E form fixed as a constant, the presence of the low-barrier hydrogen bond has the effect of lowering the energy level of the G form in $D_2O$, as illustrated by the first dashed line in the activation energy diagram of FIG. 5. This reduces the rate of capture proportionately.

However, $^{D2O}(k_{cat}/K_m) \approx 2-3$ is not what was observed with the fast substrate. This line of inquiry began when a normal solvent isotope effect on $k_{cat}$ was measured and contrasted to $^{D2O}(k_{cat}/K_m)=0.84\pm0.21$.[13] It follows that if a measured $^{D2O}(k_{cat}/K_m)$ for an aspartic protease approaches a null value, then there must be a second, inverse effect on a transition-state that offsets the mandatory normal effect arising from a low-barrier hydrogen bond in the reactant state. Indeed, a pH-independent $^{D2O}(k_{cat}/K_m)=0.85\pm0.09$ has been measured for HIV-1 protease acting on Ac-Ser-Glu-Asp-Pro-Val-Val-NH$_2$—but never published for lack of an explanation.[16] The absence of any effect of pH on this value identifies its origin as something other than a chemical step involving proton transfers.

Inverse solvent isotope effects on substrate capture are not uncommon. They have been attributed to restrictions on torsional motions of exchangeable protons as enzymes "crunch" down on substrates.[25,26] Crystallographic studies on several aspartic proteases have identified a "flap closing" associated with binding of substrates and inhibitors.[27] Therefore, equating enzyme crunch with flap closing, the activation energy diagram in FIG. 5 includes an inverse kinetic and equilibrium isotope effect on the conformational change represented by ES⇌E'S and indicated by the second dashed line. (The loss of a low-barrier hydrogen bond could itself generate an inverse solvent isotope effect, but the results of Hunkapillar & Richards show the low-barrier hydrogen bond-dependent step is clearly pH-dependent and accompanied by a normal effect.)

Conclusive evidence for this combination of offsetting isotope effects are regression analyses presented in Table II for fitting proton inventories of pepsin to the equation of Kresge:[28]

$$k_n = k_H \frac{(1-n+n\phi^T)^p}{(1-n+n\phi^R)^p} \quad (2)$$

where $k_n$ represents apparent rate constants in mixtures of D$_2$O and H$_2$O, $k_H$ is an apparent rate constant in H$_2$O, n is the fraction of deuterium in mixed isotopic waters, $\Phi^T$ is the fractionation factor for a transition-state, p is the number of protons in flight and $\Phi^R$ is a fractionation factor for a reactant-state.

TABLE II

Proton Inventories on $k_{cat}$ for Porcine Pepsin

| Form of Eq. 2 | $k_H$ | $\Phi^T$ | $\Phi^R$ | σ |
|---|---|---|---|---|
| Numerator only; p = 3 | 135 ± 6 | 0.76 ± 0.27 | — | 8.66 |
| Denominator only; p = 1 | 138 ± 3 | — | 2.19 ± 0.09 | 4.03 |
| Numerator and Denominator; p = 1 | 138 ± 2 | 1.61 ± 0.30 | 3.35 ± 0.58 | 2.41 |

Data were obtained with the control substrate, Lys-Lys-Ala-Lys-Phe-Nph-Arg-Leu, which generated $^{D2O}k_{cat}=2.02\pm0.15$.[13]

Originally, there was no reason to consider reactant-state fractionation factors, so data were fitted to the numerator of Eq. 2 only, with three protons in flight as shown in the first entry to Table II. The fitted line is less curved than the data would suggest.[13]

Given the advent of a low-barrier hydrogen bond, data were subsequently re-fitted to a denominator of Eq. 2 with a single proton, shown as the second entry in Table II. Surprisingly, a much better fit is obtained, with a curved inventory that nearly passes through the data points.

Finally, data were fitted to single protons in both numerator and denominator using the full equation, which generates a curved inventory that indeed passes through the center of the data points, accompanied by a significant decrease in sigma. The third fit provides clear evidence for a low fractionation factor in the reactant state, with $\Phi^E=1/\Phi^R=1/3.35\pm0.58=0.30\pm0.05$, and an inverse kinetic solvent isotope effect on a transition-state, $^Dk=1/\Phi^T=1/1.61\pm0.30=0.62\pm0.12$. The initial reactant state for $k_{cat}$ is ES, so the apparent $\Phi^R$ in the Kresge equation may originate in an equilibrium isotope effect, which suggests the formation and loss of the low-barrier hydrogen bond within the enzyme-substrate complex, i.e. GS⇌ES.

Figure 5:
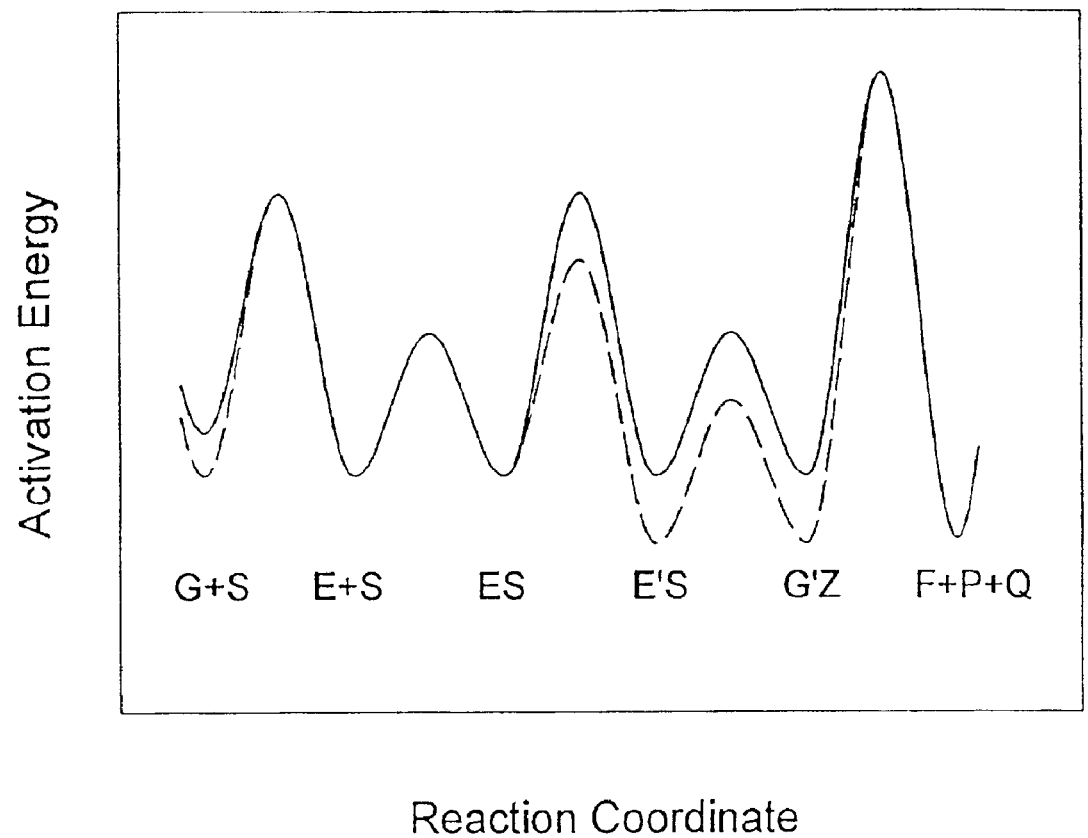
FIG. 5: Activation energy diagram for substrate capture by an asparticprotease. Steps ES→F'T→G'Z and G'Z→F'PQ→FPQ→FQ+P→F+Q were combined for simplicity. The solid line represents the energy profile in H$_2$O and was calculated using the following relative rate constants: $k_1=20$, $k_2=10$, $k_3=100$, $k_4=100$, $kd_5=10$, $k_6=10$, $k_7=100$, $k_8=100$, $k_9=1.5$. The dashed line represents energies in D$_2$O and was calculated by using the following changed rate constants: $k_1=10$, $k_5=30$, $k_9=0.5$. Hence, the first change generates $^{D2O}(k_{cat}/K_m)=2$; adding the second gives $^{D2O}(k_{cat}/K_m)=0.8$; and adding the third gives $^{D2O}(k_{cat}/K_m)=1.7$ (or 1.01 if $k_9=1$). An N-15 equilibrium isotope effect of $^{15}K_{eq}=0.95$ between E'S and G'Z is nearly fully expressed in a calculated $^{15}(k_{cat}/K_m)=0.96$.

Alternatively, the apparent $\Phi^R$ may originate in a kinetic isotope effect downstream from the virtual transition-state, i.e. F→G or G→E, that modulates the steady-state availability of the ES reactant state. It also follows that if an inverse effect is associated with flap closing, then a normal effect will be expressed subsequently on flap opening, as illustrated in FIG. 5 by a lower reactant state for G'Z in D$_2$O. Hence, there are three origins for solvent isotope effects in aspartic proteases in addition to those arising from chemical steps.

The Chemical Mechanism:

Previously proposed chemical mechanisms to account for the action of aspartic proteases have one of the active-site carboxyl groups protonated. This protonated carboxyl groups acts as a general acid to donate its proton to the substrate scissile carbonyl. In these mechanisms, the other active-site carboxyl group is unprotonated, and acts as a general base to accept a proton from a water molecule.[6] But the low-barrier hydrogen bond ties up the general acid proton and thus rules out these proposed chemical mechanisms.

Moreover, Piana & Carloni's model in FIG. 1 not only has the low-barrier hydrogen bond holding the carboxyls in a co-planar configuration, it also has the water molecule held in position via hydrogen bonds to the oxygen atoms opposite the low-barrier hydrogen bond. The water must be near the scissile bond, thus placing the low-barrier hydrogen bond proton out of the reach of the substrate during catalysis.

Figure 6A:
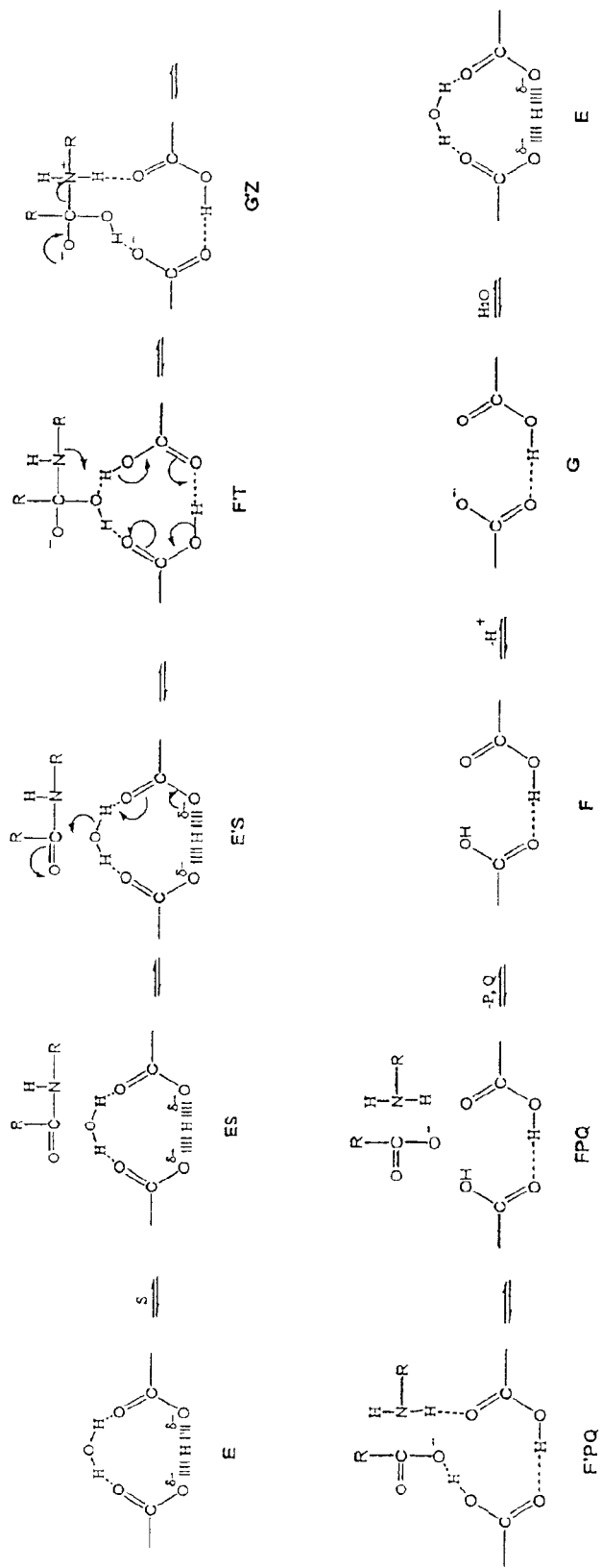
FIGS. 6A, 6B and 6C: Kinetic and chemical isomechanism of an aspartic protease. The order of product release is not designated and release of products is shown as a single step.
Figure 6B:
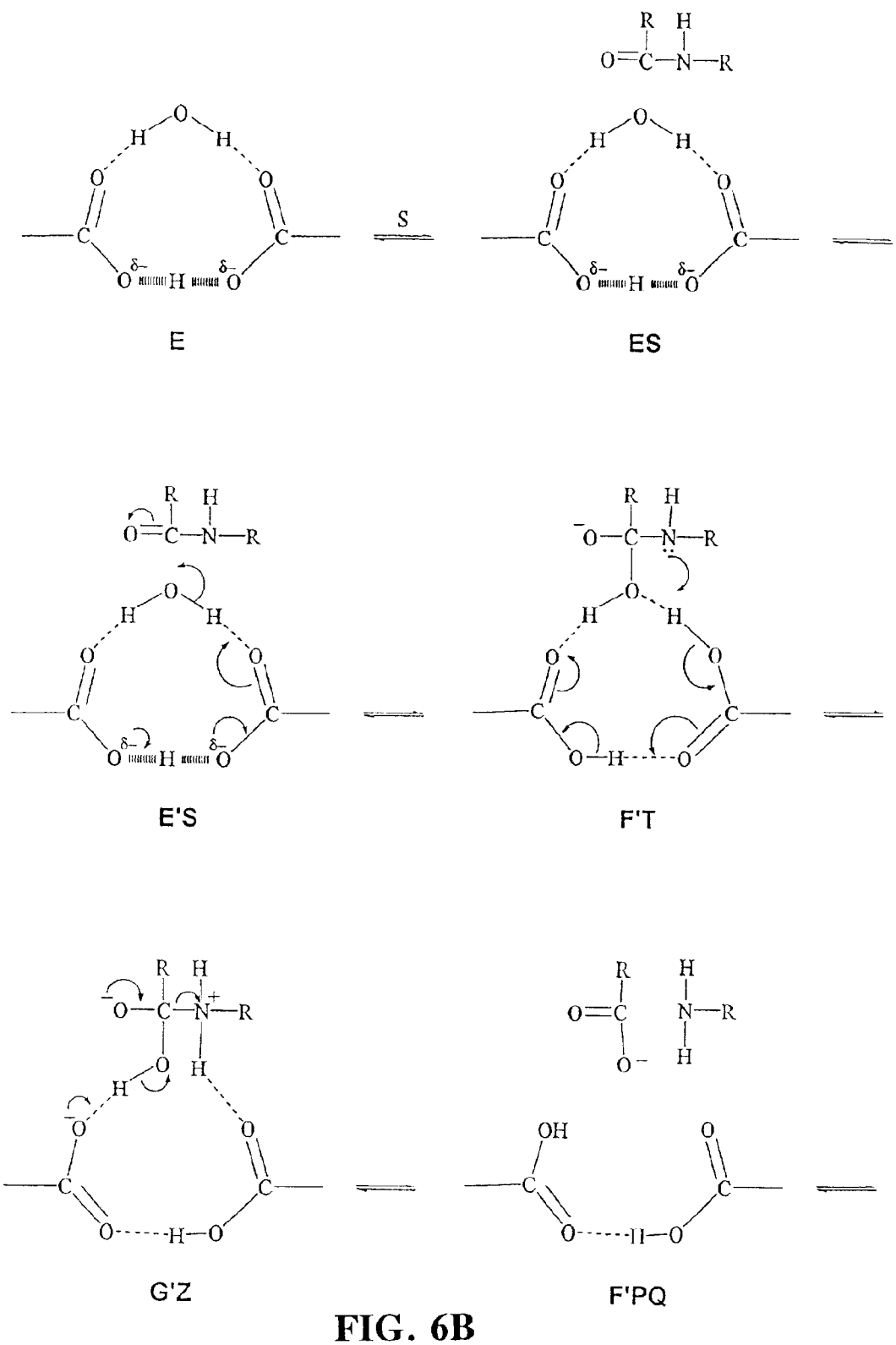
Figure 6C:
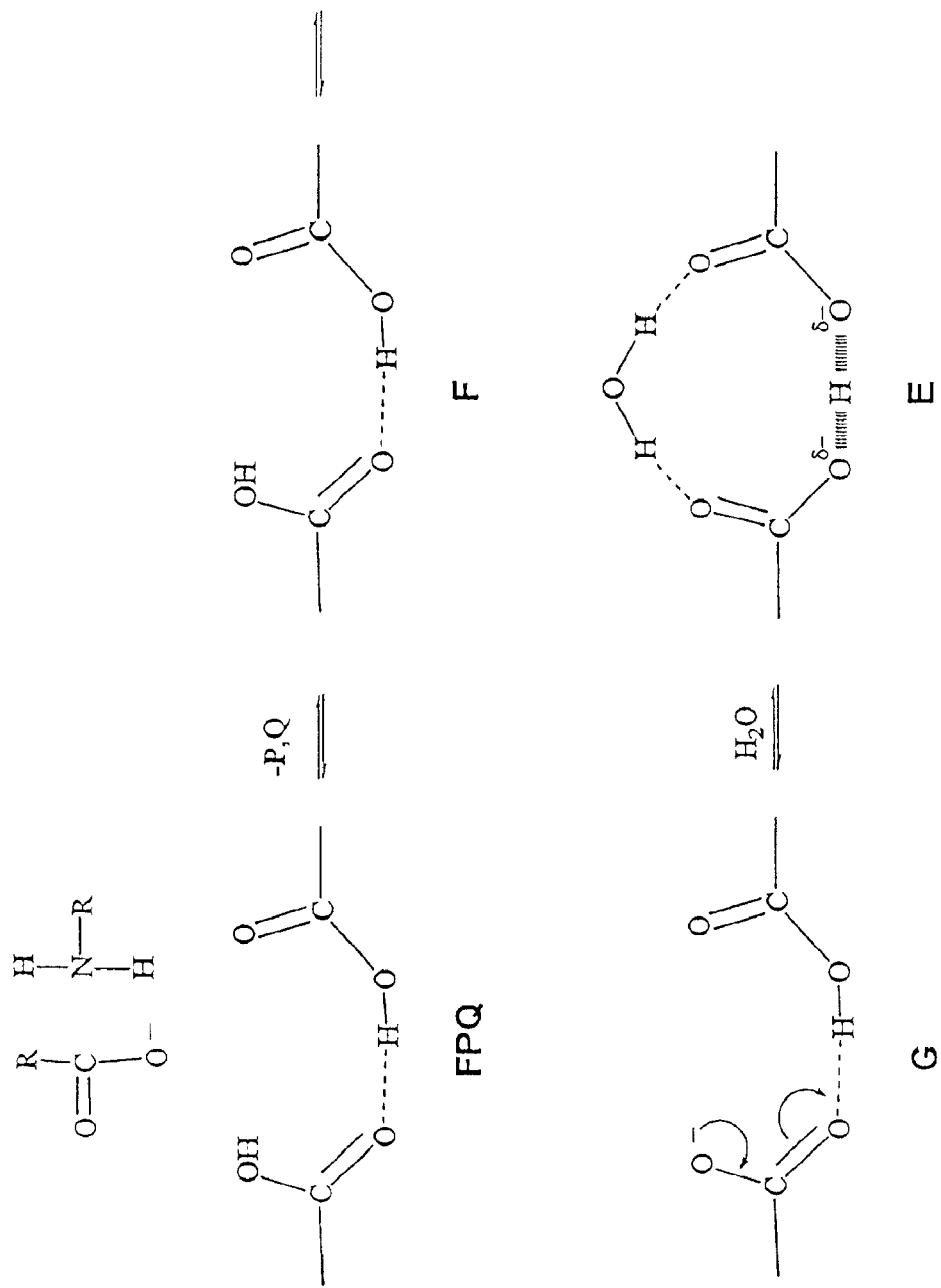

Starting with the cyclized active-site structure shown in FIG. 1 (as enzyme form E), FIGS. 6A, 6B, and 6C show a proposed chemical mechanism consistent with the foregoing kinetic data. After substrate binding and flap closing (designated by E→ES→E'S in FIGS. 6A and 6B), there occurs a counterclockwise movement of electrons within the cyclic active site and extending through the scissile carbonyl. This electronic motion concomitantly moves two protons clockwise and generates a tetrahedral intermediate bound to a di-protonated F'T form of enzyme.

The next step, a clockwise movement of electrons around the cyclic active site, moves two protons counterclockwise and generates the zwitterion intermediate bound to a mono-protonated G'Z form of enzyme. Finally, collapse of the zwitterion cleaves the scissile bond, destroys the co-planarity of the carboxyls, and leaves the enzyme in the FPQ form. That completes the chemistry with regards to the substrate, but not for the enzyme.

Flap-opening and product dissociation releases free enzyme in the di-protonated F form, the form that catalyzes transpeptidation reactions (FIGS. 6A and 6C). To complete a turnover, the F form must be de-protonated, re-hydrated, and allowed to restructure the 10-atom cyclic active site with the low-barrier hydrogen bond. These three steps (shown as two in FIGS. 6A and 6B) constitute the iso segment of the kinetic mechanism, the first and third of which should express normal solvent isotope effects with linear inventories.

Both effects contribute to increased concentration of F during turnovers in $D_2O$. This might generate an inverse isotope effect on the onset of pepstatin binding if pepstatin bound only to the F form. The observed normal effect is most likely due to some pepstatin binding to the G form as well, followed by an isotopically-sensitive protonation as binding tightens in the GI→FI step.

Energetics and Hydrogen Tunneling:

Regarding the catalytic strategy of how low-barrier hydrogen bonds provide rate acceleration, Cleland[7] writes: "The principle here is simple. A weak hydrogen bond in the ground state becomes a low-barrier hydrogen bond in the transition-state or in a transient intermediate. The energy released in forming the low-barrier hydrogen bond is used to help the reaction that forms it, thus lowering the activation barrier for the reaction."

In stark contrast, the chemical mechanism in FIG. 6 runs contrary to Cleland's principle because a low-barrier hydrogen bond is lost on the way to F'T. From an enthalpic point of view, this will have the effect of raising the activation barrier and slowing the rate. This energy deficit could be offset by a loss in entropy as the tightly structured coplanar carboxyls, trapped water molecule, and tertiary carbonyl give way, but it is difficult to see how the one could do more than offset the other and thus provide any rate acceleration.

Figure 7:
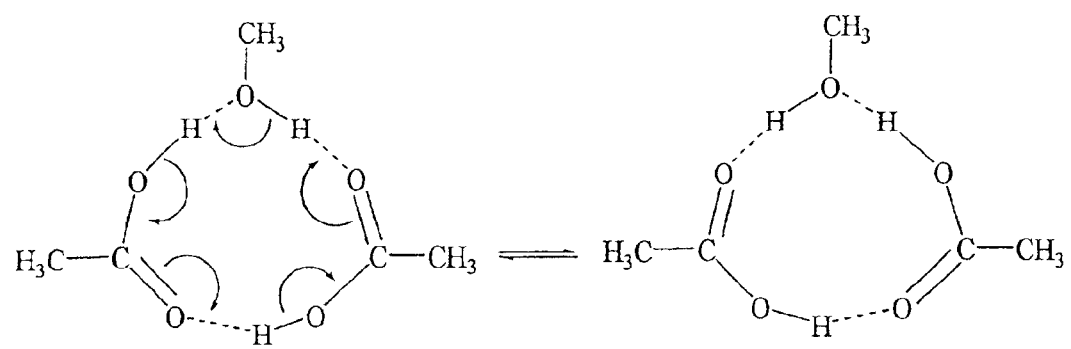
FIG. 7: Synchronous intramolecular cyclic proton transfers between methanol and acetic acid in tetrahydrofuran; after Gerritzen and Limbach.[29]
Figure 8:
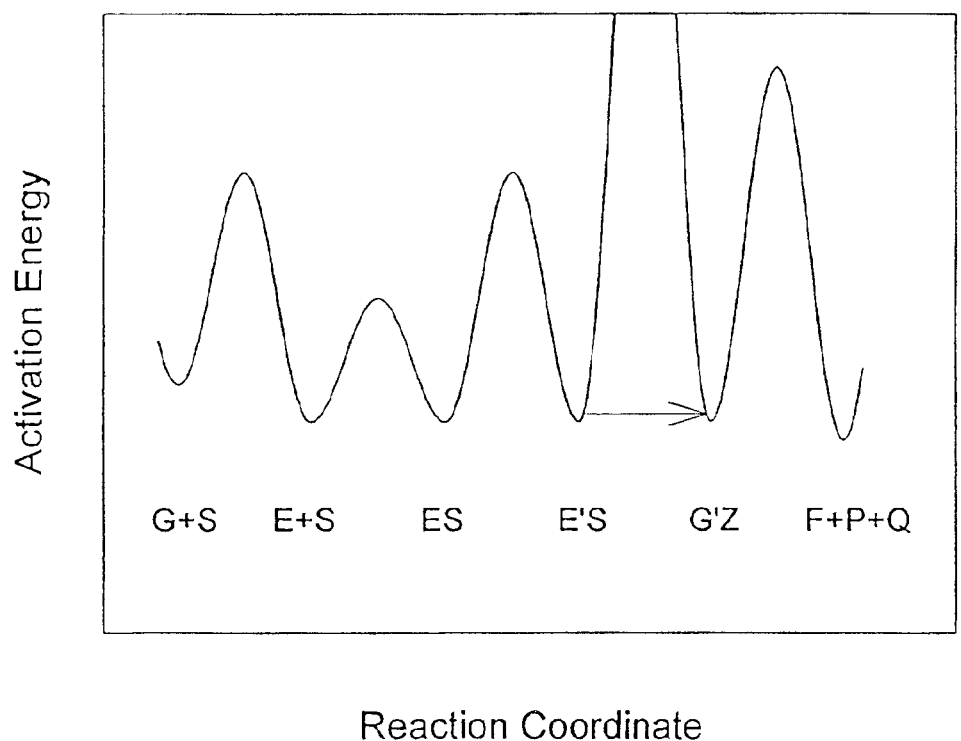
FIG. 8: Activation energy diagram for substrate capture with hydrogen tunneling. Steps E'S→F'T→G'Z and G'Z→F'PQ→FPQ→FQ+P→F+Q again were combined only now the former is represented with an insurmountable barrier. Rate acceleration is accomplished by means of ground-state hydrogen tunneling as indicated by the horizontal arrow.

Gerritzen and Limbach[29] provide some aid with their characterization of a hydrogen-bonded complex between acetic acid and methanol in tetrahydrofuran, illustrated in FIG. 7. It bears an uncanny resemblance to the co-planar carboxyl complex of Piana & Carloni. In a non-polar environment—not unlike pepsin's active site—a pair of carboxyls and a hydroxyl spontaneously form a cyclic, 10-atom complex. Within this complex, covalent single and double bonds rapidly exchange positions, reminiscent of aromaticity. But included in the cyclic exchange are covalent and non-covalent hydrogen bonds. Hence, the synchronous cyclic exchange includes rapid but formal and measurable proton transfers ($k \approx 3000$ $s^{-1}$ at 298° K.). As measured by proton NMR, the deuterium isotope effect for a single proton transfer is $k_{HHH}/k_{HHD}=2.2$ at 298° K., and for three is $k_{HHH}/k_{DDD}=(2.3)^3$, which means that the rule of the geometric mean is obeyed. There are no isotope effects on isotope effects and no coupled motion, and each transfer occurs independently. Importantly, apparent energies of activation for H and D are essentially identical, leaving differences in the Arrhenius pre-exponentials as the primary, if not sole, origin of kinetic isotope effects. These data provide strong evidence that the cyclic exchange proceeds by means of reactant-state hydrogen tunneling.

Ramifications:

Aspartic proteases can hydrolyze peptide bonds quickly and easily by using synchronous cyclic proton transfers and reactant-state tunneling, but then they must be "reloaded" (cleared of products, deprotonated and rehydrated) and "cocked" (the low-barrier hydrogen bond reformed) and the reloading and cocking of the enzyme is the slower reaction segment with good substrates. Thus, tracking the reformation of the low-barrier hydrogen bond, using NMR, provides a means for evaluating the efficacy of putative aspartic protease inhibitors.

This mechanistic hypothesis is timely in that hydrogen tunneling is a new candidate for explaining other enzymatic rate accelerations.[31] Given the recent discoveries that the endothelin converting enzyme[32] implicated in coronary artery disease, the saps[33] identified as virulence factors of fungal infections, and the beta-site Alzheimer's amyloid precursor protein cleaving enzyme[34] are all aspartic proteases, we are assured that a keen interest in the mechanisms of this family of enzyme will continue.

Obviously, the design and synthesis of mechanism-based inhibitors has a greater likelihood of success if one has the correct mechanism. Success with transition-state analog inhibitors rests on the tighter binding of substrates within a stabilized transition-state, but if rate acceleration is accomplished by some other means, then this design should fail. Looking to new inhibitor designs, given the energy needed to break a low-barrier hydrogen bond, one might expect to achieve tighter binding by developing inhibitors that do not cause the bond to be broken.

Assay of Aspartic Protease Inhibitors:

Thus, the present invention is directed primarily to a method for assaying the efficacy of a putative aspartic protease inhibitor or modulator. The assay comprises the steps of first exposing or contacting the putative inhibitor or modulator to an aspartic protease under study (in the presence and/or absence of substrate) in a medium and under conditions wherein the enzyme is active. Then, the presence, absence, and/or electronic character of a low-barrier hydrogen bond is measured to determine whether the low-barrier hydrogen bond is broken by the inhibitor's or modulator's interaction with the enzyme. The preferred means to measure the presence, absence, and/or electronic character of the low-barrier hydrogen bond is via proton NMR. Other alternative or additional methods may be used to track the low-barrier hydrogen bond, including UV, IR, and visible spectrophotometry, and/or mass spectrometry. Fluorescence spectrometry may be used, as well as pH profiling and solvent isotope effects.

In each of these approaches, the enzyme under study and the putative or known inhibitor are contacted with one another under conditions where the enzyme is active. The activity of the enzyme can then be monitored, along with the effects the inhibitor has on the electronic character of the low-barrier hydrogen bond. Parallel control experiments can also be run in which the enzyme is assayed in the absence of the inhibitor.

When measuring the character of the low-barrier hydrogen bond via pH profiling, the activity of the enzyme in the presence of the inhibitor is plotted as a function of pH. Inhibitors that display exclusive or preferential binding to a mono-protonated form of the enzyme, and hence act upon the low-barrier hydrogen bond, will generally display a bell-shaped (i.e., gaussian) pH profile (as opposed to a half-bell or flat pH profile).

Steady-state kinetic assays, using any of the spectrophotometric methods listed previously, can be performed in the same fashion as discussed in Marcinkeviciene et al. (2002) (JBC Papers in Press, manuscript M203120200). Briefly, assays can be performed and tracked by fluorescence spectroscopy (excitation at 340 nm, emission at 490 nm) upon the cleavage of a synthetic substrate. (Many such substrates are available commercially, such as from Bachem, Bubendorf, Switzerland.) Assays can be performed in conventional 96-well plates using a microplate spectrofluorimeter, such as a SPECTRAmax GEMINI XS-brand device, available from Molecular Devices.

Typical conditions would include a starting reagent mixture containing 0.1 ml of 50 mM acetate buffer (of varying pHs, say pH 5.0 and 3.0), and 40 mM of enzyme to be assayed. This solution would then be mixed with 0.004 ml of the inhibitor to be tested in DMSO. The reaction is then initiated by adding 0.1 ml of 0.02 mM substrate in the same acetate buffer as the enzyme. The reaction is then tracked by the chosen method to determine the effect the inhibitor has on the electronic character of the low-barrier hydrogen bond.

As noted above, preferred inhibitors or modulators are those that have a desirable effect on the aspartic protease, without breaking the low-barrier hydrogen bond present at the active site.

References

1. Gillespie, A. L. *The Natural History of Digestion*, London, 1898.
2. Northrop, J. H. Crystalline pepsin I. Isolation and tests for purity, *J. Gen. Physiol.* 1930, 739–766.
3. Sörensen, S. P. L. Enzymstudien II. Mitteilung. Über die Messung und die Bedeutung der Wasserstoffionen— konzentration bei enzymatischen Prozessen, *Biochem. Zeit.* 1909, 21, 201–304.
4. Knowles, J. R. On the mechanism of action of pepsin. *Phil. Trans. Royal Soc. Lon.—Ser. B: Biol. Sci.* 1970, 257, 135–46.
5. Piana, S.; Carloni, P. Conformational flexibility of the catalytic asp dyad in HIV-1 protease: an ab initio study on the free enzyme. *Prot. Struct. Func. Gen.* 2000, 39, 26–36.
6. Meek, T. D. Catalytic mechanisms of the aspartic proteinases. In *Comprehensive Biological Catalysis: a Mechanistic Reference,* Sinnott, M., Ed., Academic Press: San Diego, 1998; Chapter 8.
7. Cleland, W. W. Low barrier hydrogen bonds in enzymatic catalysis. *Arc. Biochem. Biophys.* 2000, 382, 1–5.
8. Smith, R., Brereton, I. M., Chai, R. Y., Kent, S. B., Ionization states of the catalytic residues in HIV-1 protease. *Nature Struc. Biol.* 1996, 3,946–50.
9. Piana, S, Sebastiani, D., Carloni, P., Parrinello, M. An ab-initio molecular dynamics-based assignment of the protonation state of pepstatin A/HIV-1 protease cleavage site. *J. Am. Chem. Soc.* 2001, manuscript submitted.
10. Hunkapillar, M . W., Richards, J. H. Studies on the catalytic mechanism of pepsin using a new synthetic substrate. *Biochemistry.* 1972, 273, 2829–2839.
11. Quinn, D. M., Sutton, L. D. Theoretical basis and mechanistic utility of solvent isotope effects. In *Enzyme Mechanism from Isotope Effects,* P. F. Cook, editor. CRC Press, 1991, 73–126.
12. Hyland, L. J., Tomaszek, T. A., Jr., and Meek, T. D. Human immunodeficiency virus HIV-1 protease. 2. Use of pH rate studies and solvent kinetic isotope effects to elucidate details of chemical mechanism. *Biochemistry,* 1991, 30, 8454–8463.
13. Rebholz, K. L., Northrop, D. B. Slow step after bond-breaking by porcine pepsin identified using solvent deuterium isotope effects, *Biochem. Biophys. Res. Commun.* 1991, 176, 65–69.
14. Cho, Y. K., Rebholz, K. L., Northrop, D. B. Solvent isotope effects on the onset of inhibition of porcine pepsin by pepstatin. *Biochemistry.* 1994, 33, (32):9637–42.
15. Rebholz, K. L., *Enzymatic iso mechanisms: alanine racemase, fumarase, and aspartic proteinases*. University of Wisconsin-Madison, 1993.
16. Rodriguez, E. J., Meek, T. D. (Unpublished results).
17. Neumann, H., Levin, H., Berger, A., Katchalski, E. Pepsin-catalyzed transpeptidation of the amino-transfer type. *Biochem. J.* 1959 , 73, 33–41
18. Neumann, H., Knowles, J. R. Acyl- and amino-transfer routes in pepsin-catalyzed reactions. *J. Am. Chem. Soc.* 1975, 97, 3557–3559.
19. Cho, Y-K., Northrop, D. B. Transpeptidation by porcine pepsin catalyzed by a noncovalent intermediate unique to its iso-mechanism, *J. Biol. Chem.* 1999, 273, 24305–24308.
20. Hofmann, T., Blum, M., Cunningham, A. Studies on the mechanism of action of penicillopepsin. *Adv. Exp. Med. Biol.* 1991, 608, 243–54.
21. Balbaa, M., Blum, M., Hofmann, T. Mechanism of pepsin-catalyzed amino-transpeptidation reactions. *Int. J. Biochem.* 1994, 26, 35–42.
22. Zhao, Q., Abeygunawardana, C., Gittis, A. G., Mildvan, A. S. Hydrogen bonding at the active site of 5-3-ketosteroid isomerase. *Biochemistry,* 1997, 36, 14616–14626.
23. Mihalyi, E. *Application of Proteolytic Enzymes to Protein Structure Studies*. CRC Press, Cleveland, Ohio, 1972, pp. 39–101.
24. Northrop, D. B. On the meaning of $K_m$ and $V_{max}/K_m$ in enzyme kinetics. *J. Chem. Ed.* 1998. 75, 1153–57.
25. Cleland, W. W. The use of isotope effects in the detailed analysis of catalytic mechanisms of enzymes. *Bioorg. Chem.* 1987, 15, 283–302.
26. Cho, Y. K., Northrop, D. B. Effects of high pressure on solvent isotope effects of yeast alcohol dehydrogenase. *Biophys. J.* 2000, 79, 1621–1628.
27. Davies, D. R. The structure and function of the aspartic proteinases. *Annu. Rev. Biophys. Biophys. Chem.* 1990, 19, 189–215.
28. Kresge, A. J. Solvent isotope effect in $H_2O$-$D_2O$ mixures. *Pure Applied Chem.* 1964 8, 243–258.
29. Gerritzen, D., Limbach, H. H., Kinetic isotope effects and tunneling in cyclic double and triple proton-transfer between acetic acid and methanol in tetrahydrofuran studied by dynamic H-1 and H-2 NMR spectroscopy- *JACS* 1984, 869–879.
30. Rodriguez, E. J., Angeles, T. S., Meek, T. D. Use of nitrogen-15 kinetic isotope effects to elucidate details of the chemical mechanism of human immunodeficiency virus 1 protease. *Biochemistry* 1993, 32, 12380–12385.
31. Sutcliffe, M. J., Nigel S. Scrutton, N. S. Enzyme catalysis: over-the-barrier or through-the-barrier? *Trends Biochem. Sci.* 2000, 25, 405–408.
32. Turner, A. J., Murphy, L. J., Molecular pharmacology of endothelin converting enzymes. *Biochem. Pharmacol,* 1996, 51, 91–102.
33. Goldman, R. C., Frost, D. J., Capobianco, J. O., Kadam, S., Rasmussen, R. R., Abad-Zapatero C. Antifungal drug targets: *Candida* secreted aspartyl protease and fungal wall beta-glucan synthesis. *Infect. Ag. Dis.* 1995, 4, 228–47.
34. Vassar, R., Bennett, B. D., Babu-Khan, S., Kahn, S., Mendiaz, E. A., Denis, P., Teplow, D. B., Ross, S., Amarante, P., Loeloff, R, Luo, Y., Fisher, S., Fuller, J., Edenson, S., Lile, J., Jarosinski, M, A., Biere, A, L., Curran, E., Burgess, T., Louis, J. C., Collins F., Treanor, J., Rogers, G., Citron, M. Beta-secretase cleavage of Alzheimer's amyloid precursor protein by the transmembrane aspartic protease BACE, *Science,* 1999, 286, 735–41.

What is claimed is:

1. A method for evaluating enzyme inhibitory activity of a known or putative inhibitor or modulator of an enzyme, the enzyme having a low-barrier hydrogen bond present in an active site of the enzyme, the method comprising:

(a) contacting a known or putative enzyme inhibitor or modulator with an enzyme having an existing low-barrier hydrogen bond present in an active site of the enzyme in the absence of the known or putative enzyme inhibitor, in a medium and under conditions wherein the enzyme is active; and then (b) measuring a presence, absence, or electronic character of the low-barrier hydrogen bond present in the active site of the enzyme when the enzyme is in contact with the known or putative enzyme inhibitor, whereby the enzyme inhibitory activity of the inhibitor or modulator is evaluated.

2. The method of claim 1, wherein in step (a), the known or putative inhibitor or modulator is contacted with an aspartic protease.

3. The method of claim 1, wherein in step (a), the known or putative inhibitor or modulator is contacted with the enzyme in the presence of a known substrate for the enzyme.

4. The method of claim 1, wherein in step (a), the known or putative inhibitor or modulator is contacted with the enzyme in the absence of a known substrate for the enzyme.

5. The method of claim 1, wherein in step (b), the low-barrier hydrogen bond is measured to determine whether the lower-barrier hydrogen bond is broken by the inhibitor's or modulator's contact with the enzyme.

6. The method of claim 1, wherein in step (b), the presence, absence, or electronic character of the low-barrier hydrogen bond is measured by a means for measuring selected from the group consisting of proton NMR spectroscopy, UV spectrophotometry, IR spectrophotometry, visible spectrophotometry, fluorescence spectrometry, mass spectrometry, pH profiling, and by measuring solvent isotope effects.

7. The method of claim 1, wherein in step (b), the presence, absence, or electronic character of the low-barrier hydrogen bond is measured by proton NMR spectroscopy.

8. A method for evaluating enzyme inhibitory activity of a known or putative inhibitor or modulators of an aspartic protease, the method comprising:

(a) contacting a known or putative inhibitor or modulator of an aspartic protease with an aspartic protease having an existing low-barrier hydrogen bond present in an active site of the aspartic protease in the absence of the known or putative enzyme inhibitor, in a medium and under conditions wherein the aspartic protease is active; and then (b) measuring a presence, absence, or electronic character of the low-barrier hydrogen bond present in the active site of the aspartic protease when the aspartic protease is in contact with the known or putative enzyme inhibitor, whereby the enzyme inhibitory activity of the inhibitor or modulator is evaluated.

9. The method of claim 8, wherein in step (a), the known or putative inhibitor or modulator is contacted with the aspartic protease in the presence of a known substrate for the aspartic protease.

10. The method of claim 8, wherein in step (a), the known or putative inhibitor or modulator is contacted with the aspartic protease in the absence of a known substrate for the aspartic protease.

11. The method of claim 8, wherein in step (b), the low-barrier hydrogen bond is measured to determine whether the lower-barrier hydrogen bond is broken by the inhibitor's or modulator's contact with the aspartic protease.

12. The method of claim 8, wherein in step (b), the presence, absence, or electronic character of the low-barrier hydrogen bond is measured by a means for measuring selected from the group consisting of proton NMR spectroscopy, UV spectrophotometry, IR spectrophotometry, visible spectrophotometry, fluorescence spectrometry, mass spectrometry, pH profiling, and by measuring solvent isotope effects.

13. The method of claim 8, wherein in step (b), the presence, absence, or electronic character of the low-barrier hydrogen bond is measured by proton NMR spectroscopy.

14. A method for evaluating enzyme inhibitory activity of a known or putative inhibitor or modulators of an enzyme having an Enzyme Classification of EC 3.4.23.x, the method comprising:

(a) contacting a known or putative enzyme inhibitor or modulator with an enzyme having an Enzyme Classification of EC 3.4.23.x, where x is an integer, wherein the enzyme includes an existing low-barrier hydrogen bond present in an active site of the enzyme in the absence of the known or putative enzyme inhibitor, in a medium and under conditions wherein the enzyme is active; and then (b) measuring a presence, absence, or electronic character of the low-barrier hydrogen bond present in the active site of the enzyme using proton NMR, when the enzyme is in contact with the known or putative enzyme inhibitor, whereby the enzyme inhibitory activity of the inhibitor or modulator is evaluated.

15. The method of claim 14, wherein in step (a), the known or putative inhibitor or modulator is contacted with the enzyme in the presence of a known substrate for the enzyme.

16. The method of claim 14, wherein in step (a), the known or putative inhibitor or modulator is contacted with the enzyme in the absence of a known substrate for the enzyme.

17. The method of claim 14, wherein in step (b), the low-barrier hydrogen bond is measured to determine whether the lower-barrier hydrogen bond is broken by the inhibitor's or modulator's contact with the enzyme.

* * * * *